United States Patent
Reuveni et al.

(10) Patent No.: US 8,058,309 B2
(45) Date of Patent: Nov. 15, 2011

(54) PROTEIN KINASE MODULATORS AND THERAPEUTIC USES THEREOF

(75) Inventors: Hadas Reuveni, Har Adar (IL); Alexander Levitzki, Jerusalem (IL); Lilach Steiner, Mevaseret Zion (IL); Revital Sasson, Gan-yavne (IL); Iris Ben-David, Ashdod (IL); Avi Weissberg, Rishon le Zion (IL)

(73) Assignee: Novotyr Therapeutics Ltd., Kiryat Shmona (IL)

( * ) Notice: Subject to any disclaimer, the term of this patent is extended or adjusted under 35 U.S.C. 154(b) by 120 days.

(21) Appl. No.: 12/517,278

(22) PCT Filed: Dec. 4, 2007

(86) PCT No.: PCT/IL2007/001494
§ 371 (c)(1),
(2), (4) Date: Aug. 10, 2009

(87) PCT Pub. No.: WO2008/068751
PCT Pub. Date: Jun. 12, 2008

(65) Prior Publication Data
US 2010/0056635 A1   Mar. 4, 2010

Related U.S. Application Data

(60) Provisional application No. 60/872,511, filed on Dec. 4, 2006.

(51) Int. Cl.
*A61K 31/36* (2006.01)
*A61K 3/135* (2006.01)
*C07C 319/00* (2006.01)
*C07C 321/00* (2006.01)

(52) U.S. Cl. .......... 514/464; 514/646; 564/336; 568/47; 568/336

(58) Field of Classification Search .................. 514/464, 514/646; 564/336; 568/47, 337
See application file for complete search history.

(56) References Cited

U.S. PATENT DOCUMENTS
5,217,999 A   6/1993 Levitzki
5,773,476 A *   6/1998 Chen et al. .................... 514/620
2004/0127555 A1*   7/2004 Snow et al. .................... 514/464

FOREIGN PATENT DOCUMENTS
WO   95/24190 A1   9/1995

OTHER PUBLICATIONS

Levitzki, et al., "Tyrosine kinase inhibition: an approach to drug development", Science, 267, 1782-88, Mar. 24, 1995.*
Aaronson S. T., "Growth Factors and Cancer", Science, 254:1146-1153 (1991).
Backstrom R. et al., "Synthesis of Some Novel Potent and Selective Catechol O-Methyltransferase Inhibitors", J. Med. Chem., 32:841-846 (1989).
Berge S. M. et al., "Pharmaceutical Salts", J. Pharm. Sci., 66(1):1-19 (1977).
Blum G. et al., "Substrate Competitive Inhibitors of IGF-1 Receptor Kinase", Biochem., 39:15705-15712 (2000).
Gazit A. et al., "Tyrphostins I: Synthesis and Biological Activity of Protein Tyrosine Kinase Inhibitors", J. Med. Chem., 32:2344-2352 (1989).
Goodson J. M., "Dental Applications", Medical Applications of Controlled Release, 2:115-138 (1984).
Langer R., "New Methods of Drug Delivery", Science, 249:1527-1533 (Sep. 28, 1990).
Levitzki A. et al., Tyrphostins—Potential Antiproliferative Agents and Novel Molecular Tools, Biochem. Pharm., 40(5):913-920 (1990).
Levitzki A., "Tyrphostins: tyrosine kinase blockers as novel antiproliferative agents and dissectors of signal transduction", FASEB J., 6:3275-3282 (1992).
Levitzki A. et al., "Tyrosine Kinase Inhibition: An Approach to Drug Development", Science, 267:1782-88 (Mar. 24, 1995).
Posner I. et al., "Kinetics of Inhibition by Tyrphostins of the Tyrosine Kinase Activity of the Epidermal Growth Factor Receptor and Analysis by a New Computer Program", Mol. Pharmacol., 45:673-683 (1994).
Saudek C. D. et al., "A Preliminary Trial of the Programmable Implantable Medication System for Insulin Delivery", N. Engl. J. Med., 321:574-579 (Aug. 31, 1989).
Schlessinger J., "Signal transduction by allosteric receptor oligomerization", TIBS, 13:443-447 (Nov. 1988).
Schlessinger J. et al., "Growth Factor Signaling by Receptor Tyrosine Kinases", Neuron, 9(3): 383-391 (Sep. 1992).
Treat T. et al., "Liposome Encapsulated Doxorubicin Preliminary Results of Phase I and Phase II Trials", Liposomes in the Therapy of Infectious Disease and Cancer, Lopez- Berestein and Fidler (eds.), Liss, NY, 353-365 (1989).
Ullrich A. et al., "Signal Transduction by Receptors with Tyrosine Kinase Activity", Cell, 61:203-212 (1990).
Yaish P. et al., "Blocking of EGF-Dependent Cell Proliferation by EGF Receptor Kinase Inhibitors", Science, 242:933-935 (Nov. 11, 1988).
Yoneda T. et al., "The Antiproliferative Effects of Tyrosine Kinase Inhibitors Tyrphostins on a Human Squamous Cell Carcinoma in Vitro and in Nude Mice", Cancer Res., 51:4430-4435 (Aug. 15, 1991).

* cited by examiner

*Primary Examiner* — Susannah Chung
(74) *Attorney, Agent, or Firm* — Fennemore Craig, P.C.; Rodney J. Fuller

(57) ABSTRACT

The present invention provides new tyrphostin derivatives acting as substrate competitive protein tyrosine kinase (PTK) inhibitors and receptor tyrosine kinase (RTK) inhibitors, methods of their preparation, pharmaceutical compositions including such compounds, and methods of using these compounds and compositions, especially as chemotherapeutic agents for preventions and treatments of PTK and RTK related disorders such as metabolic, fibrotic, and cell proliferative disorders, in particular psoriasis and cancer.

14 Claims, 22 Drawing Sheets

PROTEIN KINASE MODULATORS AND THERAPEUTIC USES THEREOF

RELATED APPLICATION DATA

This application is the U.S. national stage of PCT/IL2007/001494 filed on Dec. 4, 2007, which claims priority to and benefit of U.S. Provisional Patent Application No. 60/872,511 filed on Dec. 4, 2006, the content of each of which is expressly incorporated herein in its entirety by reference hereto.

FIELD OF THE INVENTION

The present invention relates to novel tyrphostin derivatives, their preparation, pharmaceutical compositions comprising same, and their use in treatment of protein kinase related disorders.

BACKGROUND OF THE INVENTION

Protein tyrosine kinases (PTKs) are a family of enzymes, which transfer the γ-phosphate of ATP to the side chain of tyrosine residues on substrate proteins. PTKs are involved in a variety of cellular processes, including signal transduction and growth regulation. Phosphorylation of substrates by PTKs are key events in cellular signaling.

One class of PTKs are receptor tyrosine kinases (RTKs). These kinases belong to a family of transmembrane proteins and have been implicated in cellular signaling pathways. The predominant biological activity of some receptor kinases is the stimulation of cell growth and proliferation, while other receptor tyrosine kinases are involved in inhibiting growth and promoting differentiation. In some instances, a single tyrosine kinase can inhibit, or stimulate, cell proliferation depending on the cellular environment in which it is expressed (Schlessinger and Ullrich, Neuron (1992), 9(3): 383-391). RTKs include receptors for platelet-derived growth factor (PDGF), fibroblast growth factor (FGF), hepatocyte growth factor (HGF), insulin, insulin-like growth factor 1 (IGF-1), nerve growth factor (NGF), vascular endothelial growth factor (VEGF), macrophage colony stimulating factor (M-CSF) and others.

Receptor tyrosine kinases are composed of at least three domains: an extracellular glycosylated ligand binding domain, a transmembrane domain and a cytoplasmic catalytic domain that can phosphorylate tyrosine residues. Binding of a ligand to membrane-bound receptors induces the formation of receptor dimers and allosteric changes thus activating the intercellular kinase domains which further results self-phosphorylation (autophosphorylation and/or transphosphorylation) of the receptor on tyrosine residues. Receptor phosphorylation stimulates physical association of the activated receptor with target molecules. Some of the target molecules are, in turn, phosphorylated, a process which transmits the signal to the cytoplasm. The secondary signal transducer molecules generated by activated receptors, result in a signal cascade that regulates cell functions such as cell division or differentiation. Intracellular signal transduction is reviewed in Aaronson, Science (1991), 254: 1146-1153; Schlessinger, J. Trends Biochem. Sci. (1988), 13: 443-447; Ullrich and Schlessinger, Cell (1990), 61: 203-212.

Various cell proliferative disorders have been associated with defects in pathways mediated by PTKs. Enhanced activities of PTKs resulting from overexpression of the normal kinase, upregulation of ligands of receptor tyrosine kinases or activating mutations, are a hallmark of many diseases which involve cellular proliferation, including cancer. Examples of specific receptor tyrosine kinases associated with cell proliferative disorders include platelet derived growth factor receptor (PDGFR), insulin-like growth factor 1 receptor (IGF-1R), epidermal growth factor receptor (EDFR), and the related HER.

The involvement of PTKs in various diseases identifies them as targets for antiproliferative drugs. Indeed, numerous PTK blockers have been described in the literature including proposed mechanisms of action (Levitzki et al., Science (1995), 267:1782-88; Posner et al., Mol. Pharmacol. (1994), 45:673-683). Applicants have developed a family of PTK inhibitors, named tyrphostins, designed to mimic the tyrosine substrate (Levitzki et al., Science (1995), 267:1782-88; Levitzki et al., Biochem. Pharm. (1990), 40:913-920; Levitzki et al., FASEB J. (1992), 6:3275-3282; U.S. Pat. Nos. 5,217,999 and 5,773,476). The pharmacophores of these tyrphostins, and in particular tyrphostins of the benzylidene malonitril type, are the hydrophilic catechol ring and the more lipophilic substituted cyano-vinyl radical. Kinetic studies have shown that some tyrphostin compounds are pure competitive inhibitors vis-á-vis tyrosine substrates whereas for the ATP binding site they act as non-competitive inhibitors (Yaish et al., Science (1988), 242:933-935; Gazit et al., J. Med. Chem. (1989), 32:2344-2352). Nonetheless, many tyrphostins have shown competitive inhibition against both the substrate and ATP binding site (Posner et al., Mol. Pharmacol. (1994), 45:673-683).

In a related group of tyrphostins, the hydrophilic catechol ring was exchanged by lipophilic dichloro- or dimethoxy-phenyl groups, to yield EGFR kinase inhibitors, effective in the low micromolar range. (Yoneda et al., Cancer Res. (1991), 51: 4430-4435). However, there is an unmet need for tyrphostins with increased inhibitory properties.

SUMMARY OF THE INVENTION

The present invention relates to new tyrphostins compounds useful as inhibitors of protein tyrosine kinases (PTKs) in cells. These novel tyrphostin compounds show increased inhibitory properties of, but not limited to, insulin-like growth factor 1 receptor (IGF1R), platelet derived growth factor receptor (PDGFR), epidermal growth factor receptor (EGFR), and IGF1R-related insulin receptor (IR). The present invention is further directed to compounds that trigger Serine phosphorylation of the IGF1R direct substrate IRS1, thus providing long-lasting effects which enhance the inhibitory activity of these novel tyrphostins.

According to one aspect, the present invention provides compounds represented by the structure of formula 1:

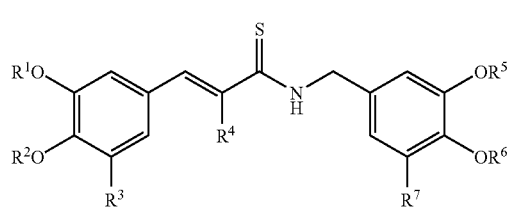

wherein
$R^1$, $R^2$, $R^5$ and $R^6$ are independently selected from H, $C_1$-$C_4$ alkyl, acyl and a functional group that gives rise to hydroxyl upon hydrolysis;

$R^3$ and $R^7$ are independently selected from H, halogen, haloalkyl and $OR^8$ wherein $R^8$ is H, $C_1$-$C_4$ alkyl, acyl or a functional group that gives rise to hydroxyl upon hydrolysis;

$R^4$ is H or CN, including salts, hydrates, solvates, polymorphs, optical isomers, geometrical isomers, enantiomers, diastereomers, and mixtures thereof.

In one embodiment, the present invention provides a compound represented by the structure of formula 1, wherein $R^3$ is halogen (e.g., F, Cl, Br or I) or haloalkyl (e.g. $CF_3$). In another embodiment, the present invention provides a compound represented by the structure of formula 1, wherein $R^1$, $R^2$, $R^5$ and $R^6$ are each H. In another embodiment, the present invention provides a compound represented by the structure of formula 1, wherein $R^7$ is hydrogen, halogen or $OR^8$ with $R^8$ being H or methyl. In one embodiment, the present invention further provides compounds of formula 1, wherein $R^4$ is H. In another embodiment, the present invention provides compounds of formula 1, wherein $R^4$ is CN.

Representative and non-limiting examples of such structures are compounds selected from the group consisting of compounds 2-18:

2
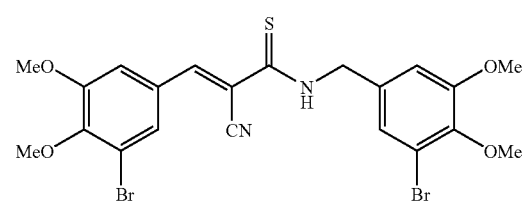

3
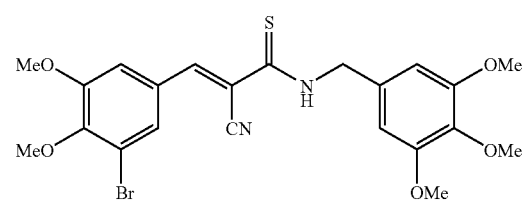

4
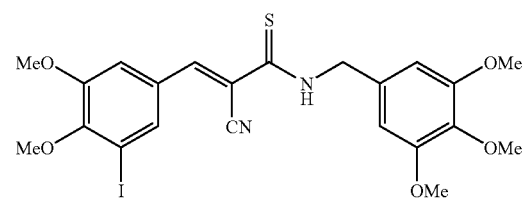

5
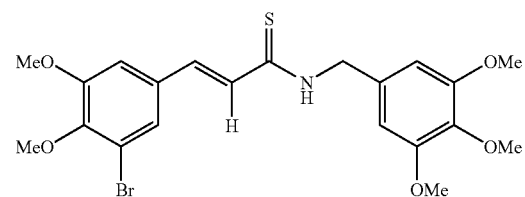

6
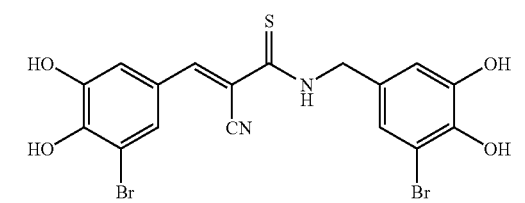

7
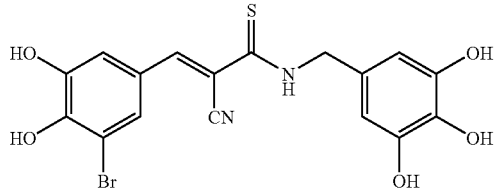

8
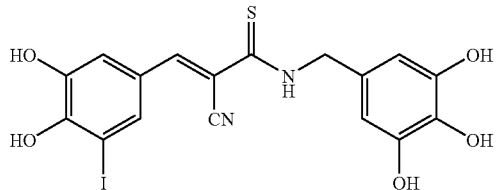

9
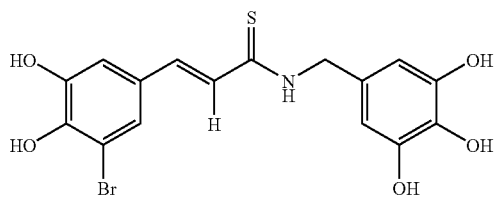

10
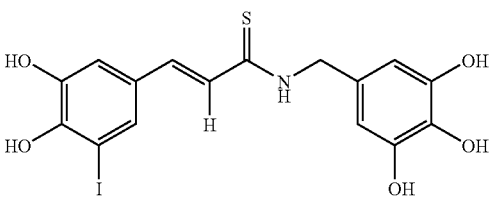

11
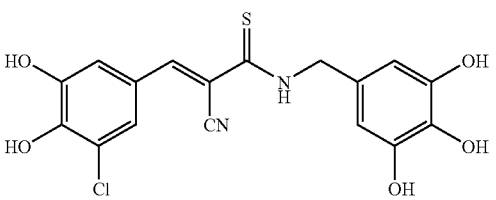

12
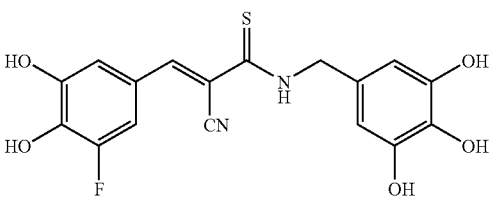

13
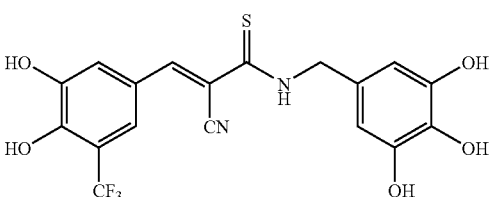

14
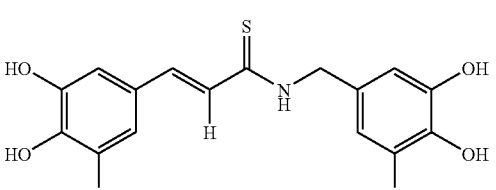

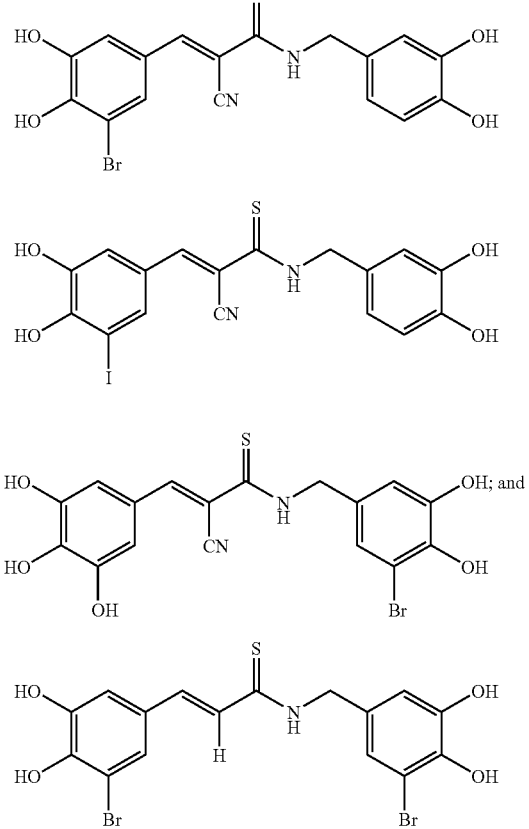

Another similar derivative is compound no. 19:

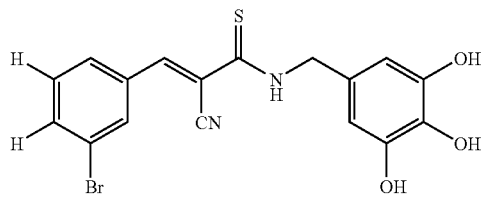

The present invention further provides pharmaceutical compositions comprising any of the compounds represented by the structure of formula 1.

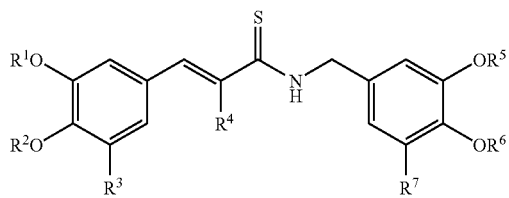

wherein $R^1$, $R^2$, $R^1$ and $R^6$ are independently selected from H, $C_1$-$C_4$ alkyl, acyl and a functional group that gives rise to hydroxyl upon hydrolysis;

$R^3$ and $R^7$ are independently selected from H, halogen, haloalkyl and $OR^8$ wherein $R^8$ is H, $C_1$-$C_4$ alkyl, acyl or a functional group that gives rise to hydroxyl upon hydrolysis;

$R^4$ is H or CN, including salts, hydrates, solvates, polymorphs, optical isomers, geometrical isomers, enantiomers, diastereomers, and mixtures thereof.

The present invention further provides a method of inhibiting a protein tyrosine kinase (PTK) comprising contacting the PTK with an effective inhibitory amount of a compound of formula 1.

The present invention further provides a method of inhibiting a protein tyrosine kinase (PTK) in a subject comprising the step of administering to the subject a therapeutically effective amount of a compound of formula 1, to inhibit a protein tyrosine kinase (PTK) in the subject. In another embodiment, the method comprises administering to the subject a pharmaceutical composition comprising a therapeutically effective amount of any of the compound of formula 1, and a pharmaceutically acceptable excipient.

The present invention further provides a method of treating or preventing a protein tyrosine kinase (PTK) related disorder in a subject comprising the step of administering to the subject a therapeutically effective amount of any of the compounds of formula 1. In another embodiment, the method comprises administering to the subject a pharmaceutical composition comprising a therapeutically effective amount of a compound of formula 1, and a pharmaceutically acceptable excipient. In one embodiment, the PTK related disorder is a cell proliferative disorder, a metabolic disorder or a fibrotic disorder. In a preferred embodiment, the PTK related disorder is cancer. In another embodiment the PTK related disorder is diabetic nephropathy.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 4A shows the inhibition of IGF1R activation and signaling in cancer cells following exposure to compound 7 in comparison to the control (compound # 20). Compound 7 induces a decrease in the tyrosine-phosphorylation of IRS1, a direct substrate of IGF1R and inhibition of IGF1-induced activation of the PKB and ERK pathways. FIG. 4B represents the dose-dependent inhibition of IGF1-induced signaling in cancer cells.

FIG. 5A shows a decrease in cellular levels of IRS1 induced by 4 hours treatment with compound 7.

FIG. 5B shows induced Serine-phosphorylation on IRS1 following 4 hours treatment with compound 7. FIG. 5C shows a long-lasting (24 hours following exposure) reduction in IRS1 levels in cancer cells.

FIG. 7A shows that cells treated with compounds 6, 7, 8 and 9 undergo apoptosis following incubation (cleaved PARP detection) with compound 6 being slightly weaker. FIG. 7B shows Ser-phosphorylation on IRS1 (detected by the shift of the IRS1 band upward) as well as a decrease in IRS1 levels induced by compounds 7, 8 and 9 in contrast to compound 6.

FIG. 9A shows that compound 7 inhibits EGFR activation in hormone-refractory prostate cancer PC3 cells, and EGF-induced phosphorylation of PKB and STAT3, a direct substrate of EGFR. FIG. 9B shows that compound 7 inhibits ligand-induced PDGFR activation and downstream signaling in NIH3T3 cells over expressing PDGFR. FIG. 9C shows that compound 7 inhibits ligand-induced Insulin receptor (IR) activation and downstream regulation in NIH3T3 cells over expressing IR.

FIG. 19A shows that compound 6 inhibits IGF1-induced IGF1R activation and signaling (auto-phosphorylation of IGF1R, the IGF1-induced tyrosine phosphorylation of IRS1 and the IGF1-induced activation of the Akt/PKB). FIG. 19B shows that compound 6 has no effect on the IRS1 levels.

FIG. 20A shows that compound 6 inhibits EGF-induced phosphorylation of EGFR and its downstream elements, STAT3 and PKB. FIG. 20B shows that protein levels are equal and no effect on STAT3, PKB or ERK was detected following treatment of PC3 cells with compound 6.

DETAILED DESCRIPTION OF THE INVENTION

Figure 1:
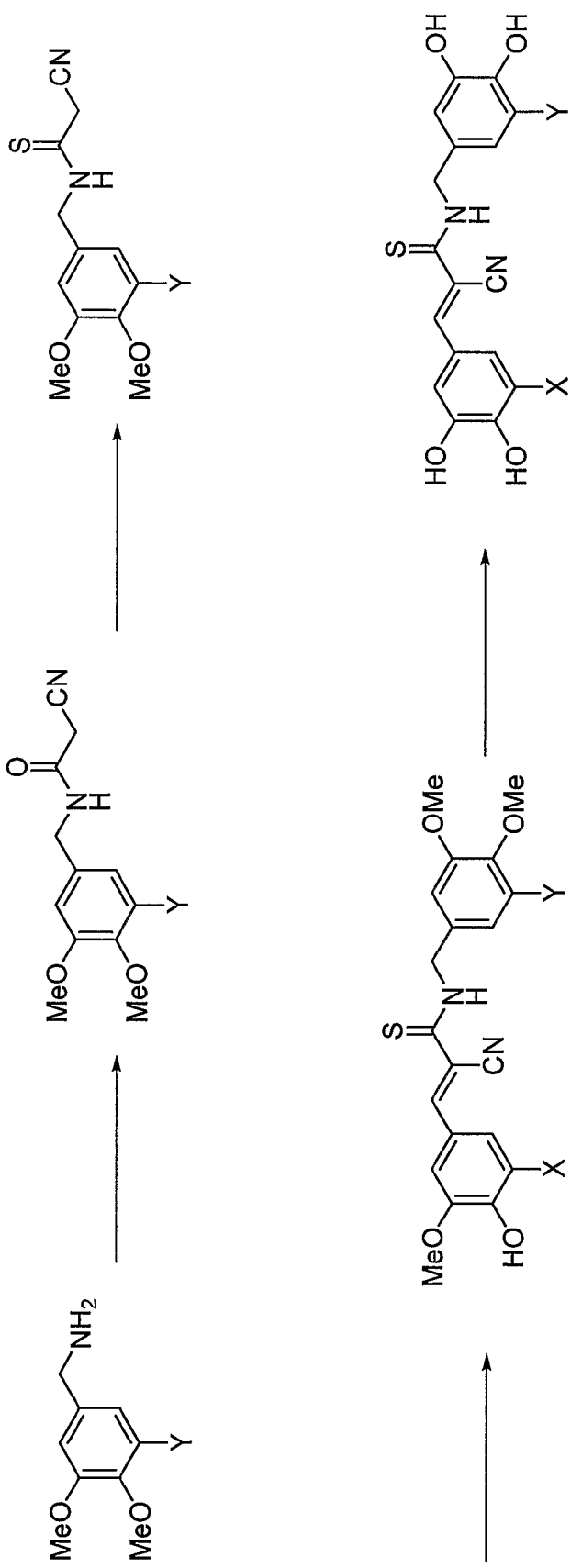
FIG. 1 Shows in schematic form a process for the synthesis of exemplary novel Tyrphostins of the invention. X and Y are independently selected from hydrogen, halogen, haloalkyl and $OR^8$ wherein $R^8$ is H, $C_1$-$C_4$ alkyl, acyl or a functional group that gives rise to hydroxyl upon hydrolysis.

The present invention relates to novel tyrphostin derivatives which are potent PTK-inhibitors. The present invention further provides methods for inhibiting PTKs, for example IGF-1 receptor (IGF1R). The compounds are useful in treating or preventing PTK-related disease states, particularly PTK-related disorders which are associated with defects in signaling pathways mediated by PTKs. Examples of diseases involving cellular proliferation are cancer and psoriasis.

The compounds of the present invention are designed to have an enhanced inhibiting potency with respect to protein tyrosine kinases (PTKs), compared with previously disclosed tyrphostin derivatives (Blum et al., *Biochem.* (2000), 39:15705-15712; U.S. Pat. Nos. 5,773,476 and 5,217,999). The applicants have surprisingly found that the introduction of additional substituents on the catechol pharmacophore greatly enhances the inhibitory potency. Furthermore, introduction of additional substituents on the second aromatic ring was also found to significantly enhance the inhibiting potency of the new compounds. In addition, it is shown that a subfamily of the described molecules triggers Serine phosphorylation of IRS1, which serves as the direct substrate of IGF-1R. Without wishing to be bound by any theory or mechanism of action, this phosphorylation may lead to decoupling of IRS1 with IGF-1R, thereby blocking IGF-1R signaling. Furthermore, this Ser-phosphorylation of IRS1 is usually accompanied by a decrease in IRS1 levels. These processes are shown to enhance the inhibitory potential of these tyrosine kinase inhibitors, thus introducing long-lasting effects.

The compounds provided by the present invention are represented by the general formula 1:

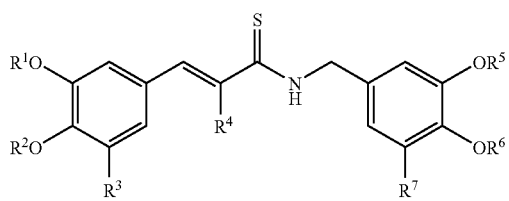

wherein $R^1$, $R^2$, $R^5$ and $R^6$ are independently selected from H, $C_1$-$C_4$ alkyl, acyl and a functional group that gives rise to hydroxyl upon hydrolysis;

$R^3$ and $R^7$ are independently selected from H, halogen, haloalkyl and $OR^8$ wherein $R^8$ is H, $C_1$-$C_4$ alkyl, acyl or a functional group that gives rise to hydroxyl upon hydrolysis;

$R^4$ is H or CN, including salts, hydrates, solvates, polymorphs, optical isomers, geometrical isomers, enantiomers, diastereomers, and mixtures thereof.

In one embodiment, the present invention provides a compound represented by the structure of formula 1, wherein $R^1$, $R^2$, $R^5$ and $R^6$ each independently H or methyl. In another embodiment, the present invention provides a compound represented by the structure of formula 1, wherein $R^3$ is halogen (e.g. F, Cl, Br, I), hydroxyl or haloalkyl (e.g. $CF_3$). In another embodiment, the present invention provides a compound represented by the structure of formula 1, wherein $R^4$ is CN. In another embodiment, the present invention provides a compound represented by the structure of formula 1, wherein $R^7$ is H, halogen or $OR^8$ with $R^8$ being H or methyl. In one embodiment, the present invention further provides a compound of formula 1, wherein $R^4$ is H. Representative and non-limiting examples of such structures are compounds selected from the group consisting of compounds 2-18:

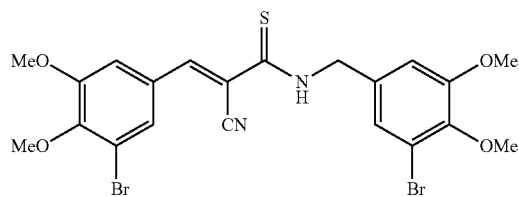

2

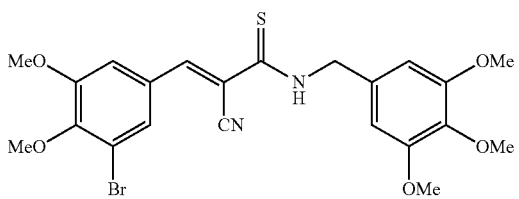

3

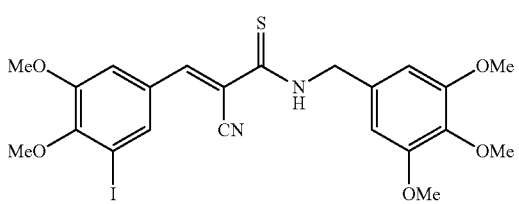

4

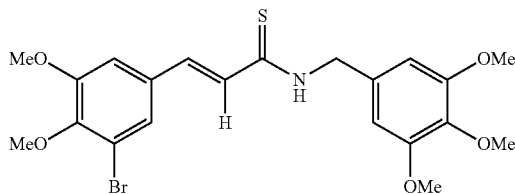

5

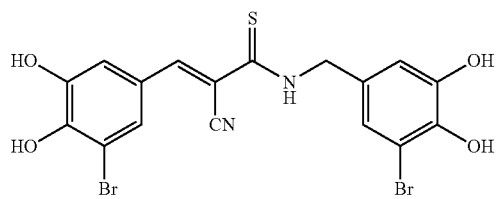

6

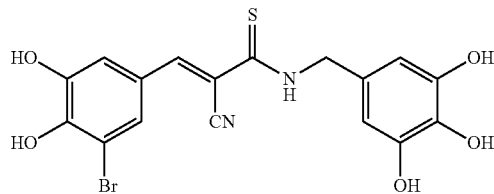

7

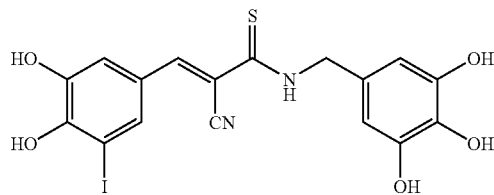

8

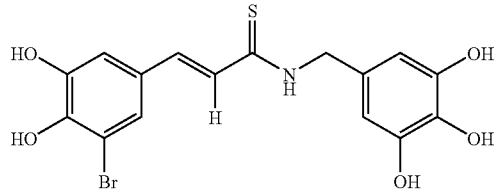

9

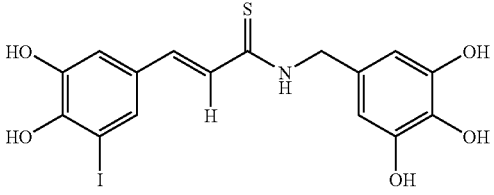

10

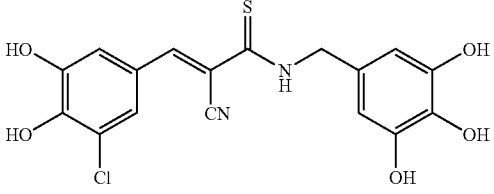

11

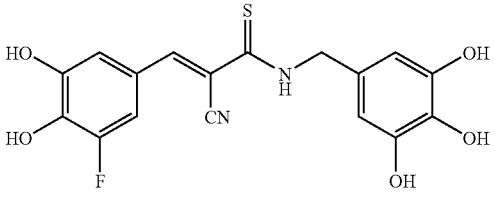

12

13

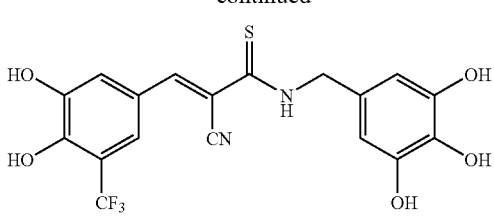

14

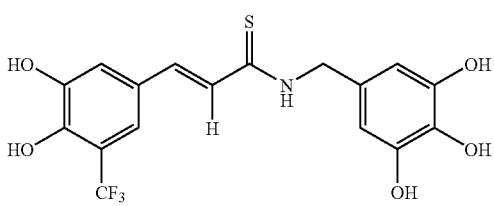

15

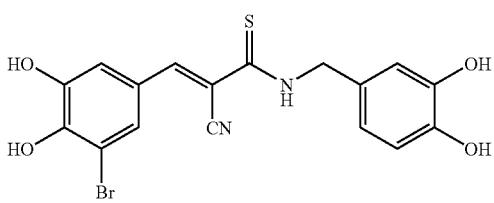

16

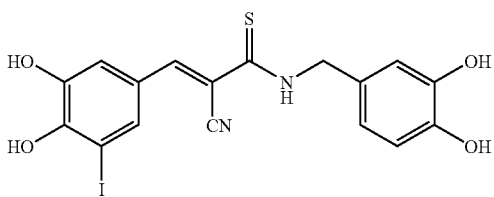

17

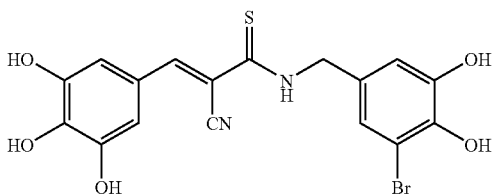

18

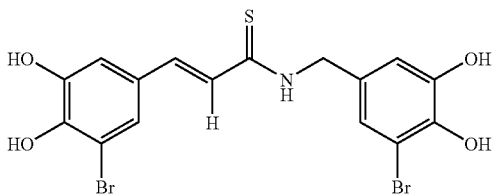

Another similar derivative is compound No. 19:

19

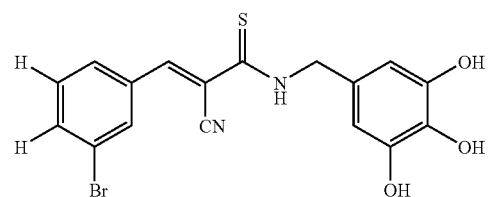

Without wishing to be bound by any theory or mechanism of action, when the hydroxyls are blocked by a methyl group, namely the compounds consist of methoxy groups in positions 1, 2, 5 & 6, the activity of the compounds is dramatically decreased in comparison to compounds having hydroxy groups at the equivalent positions. Compounds 2-5 are therefore less active in comparison to compounds 6-19 and the like.

CHEMICAL DEFINITIONS

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "hydroxy" group refers to an OH group. An "alkoxy" group refers to an —O-alkyl group wherein R is alkyl as defined above. A "thio" group refers to an —SH group. An "alkylthio" group refers to an —SR group wherein R is alkyl as defined above.

An "amino" group refers to an $NH_2$ group. An alkylamino group refers to an —NHR group wherein R is alkyl is as defined above. A dialkylamino group refers to an —NRR' group wherein R and R' are alkyl as defined above. An "amido" group refers to a —C(O)$NH_2$ group. An alkylamido group refers to an —C(O)NHR group wherein R is alkyl is as defined above. A dialkylamido group refers to an —C(O)NRR' group wherein R and R' are alkyl as defined above.

A "thioamide" group refers to a C(S)NHR, where R is either alkyl, aryl, alkylaryl or hydrogen.

The term "halogen" or "halo" as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

Examples of functional groups that give rise to hydroxyl upon hydrolysis include, but are not limited to, esters, anhydrides, carbamates, carbonates and the like. For example, when any of $R^1$, $R^2$, $R^5$ or $R^6$ is an acyl group (COR), the resulting function group is an ester (OCOR). When any of $R^1$, $R^2$, $R^5$ or $R^6$ is an amide group (CONHR), the resulting function group is a carbamate (OCONHR). When any of $R^1$, $R^2$, $R^5$ or $R^6$ is a carboxylate group (COOR), the resulting function group is a carbonate (OCOOR).

All stereoisomers of the compounds of the present invention are contemplated, either in admixture or in pure or substantially pure form. These compounds can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, 1 μL or d,l, D,L. Compounds comprising amino acid residues include residues of D-amino acids, L-amino acids, or racemic derivatives of amino acids. In addition, several of the compounds of the present invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to carboxylate salts or salts with amine nitrogens, and include salts formed with the organic and inorganic anions and cations discussed below. Further encompassed by the term are salts formed by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like.

The term "organic or inorganic cation" refers to counterions for the carboxylate anion of a carboxylate salt. The counter-ions are chosen from the alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.* (1977), 66:1-19, which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group are also contemplated.

The present invention also includes solvates of compounds of formula 1 or any of compounds 2-19 and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of compounds of formula 1 or any of compounds 2-19 and salts thereof. The term "polymorph" refers to a particular crystalline state of a substance, which can be characterized by particular physical properties such as X-ray diffraction, IR spectra, melting point, and the like.

Therapeutic Use

The present invention provides compounds and compositions effective at inhibiting protein tyrosine kinases. These compounds and compositions are potentially useful in the treatment of a diseases associated with altered or abnormal activity of protein tyrosine kinases such as enhanced activity of protein tyrosine kinases.

Thus, in one embodiment, the present invention provides a method of inhibiting a protein tyrosine kinase (PTK) comprising contacting the PTK with an effective inhibitory amount of a compound represented by any of formulas 1-19.

The present invention further provides a method of treating or preventing a protein tyrosine kinase (PTK) in a subject comprising the step of administering to the subject a therapeutically effective amount of any of the compounds represented by formulas 1-19. In another embodiment, the method comprises administering to the subject a pharmaceutical composition comprising a therapeutically effective amount of any of the compounds represented by formulas 1-19 and a pharmaceutically acceptable excipient.

The present invention further provides a method of inhibiting a protein tyrosine kinase (PTK) related disorder in a subject comprising the step of administering to the subject a therapeutically effective amount of any of the compounds represented by formulas 1-19. In another embodiment, the method comprises administering to the subject a pharmaceutical composition comprising a therapeutically effective amount of any of the compounds represented by formulas 1-19; and a pharmaceutically acceptable excipient.

A "protein tyrosine kinase" (PTK) is a protein belonging to a family of enzymes that transfer the γ-phosphate of ATP to the side chain of tyrosine residues on substrate proteins. PTKs are involved in a variety of key cellular processes, including signal transduction and growth regulation. A protein tyrosine kinase, as used herein, refers to a receptor tyrosine kinase (RTK) as well as a cellular tyrosine kinase (CTK or non-receptor tyrosine kinase). Thus the compounds of the present invention are effective at inhibiting both receptor and non-receptor protein tyrosine kinases.

A cellular tyrosine kinase (CTK or non-receptor tyrosine kinase) is an intracellular protein which takes part in signal transduction within the cell, including signal transduction to the nucleus. Examples of CTKs are the Src family of oncoproteins. A receptor tyrosine kinase (RTK) is a transmembrane protein that participates in transmembrane signaling pathways. The predominant biological activity of some receptor tyrosine kinases is the stimulation of cell growth and proliferation, while other receptor tyrosine kinases are involved in arresting growth and promoting differentiation. RTKs include the receptors for platelet-derived growth factor (PDGF), fibroblast growth factor (FGF), hepatocyte growth factor (HGF), insulin, insulin-like growth factor-1 (IGF-1), nerve growth factor (NGF), vascular endothelial growth factor (VEGF), and macrophage colony stimulating factor (M-CSF).

The term "protein tyrosine kinase related disorder" as used herein refers to a disorder characterized by abnormal or altered PTK activity. Abnormal or altered activity further refers to either (i) overexpression of PTK in cells that do not normally express PTKs; (ii) increased PTK expression leading to unwanted cell proliferation, differentiation and/or growth; or, (iii) decreased PTK expression leading to unwanted reductions in cell proliferation, differentiation and/or growth. Over-activity of PTKs refers to either amplification of the gene encoding a particular PTK or production of a level of PTK activity which can correlate with cell proliferation, differentiation and/or growth. Over-activity can also be the result of ligand independent or constitutive activation as a result of mutations such as deletions of a fragment of a PTK responsible for ligand binding.

Thus, in one embodiment, the present invention is directed to preparations containing any of the compounds represented by formulas 1-19, which modulate PTK activity signal transduction by affecting the enzymatic activity of the protein tyrosine kinases thereby interfering with the signal transduction pathways mediated by such proteins.

Examples of protein tyrosine kinase related disorders are cell proliferative disorders, metabolic disorders or fibrotic disorders and inflammation.

Examples of cell proliferative disorders which are mediated by protein tyrosine kinases are cancer, psoriasis, diabetic nephropathy, blood vessel proliferative disorders, and mesangia cell proliferative disorders.

Cancer is a disorder in which a population of cells has become, in varying degrees, unresponsive to the control mechanisms that normally govern proliferation and differentiation. Cancer refers to various types of malignant neoplasms and tumors, including metastasis to different sites. Nonlimiting examples of cancers which can be treated by any of the compounds represented by formulas 1-19 are brain, ovarian, colon, prostate, kidney, bladder, breast, lung, oral and skin cancers which exhibit altered activity of PTK. Specific examples of cancers which the compounds of the present invention are effective at treating or preventing are: adenocarcinoma, adrenal gland tumor, ameloblastoma, anaplastic tumor, anaplastic carcinoma of the thyroid cell, angiofibroma, angioma, angiosarcoma, apudoma, argentaffinoma, arrhenoblastoma, ascites tumor cell, ascitic tumor, astroblastoma, astrocytoma, ataxia-telangiectasia, atrial myxoma, basal cell carcinoma, benign tumor, bone cancer, bone tumor, brainstem glioma, brain tumor, breast cancer, Burkitts lymphoma, carcinoma, cerebellar astrocytoma, cervical cancer, cherry angioma, cholangiocarcinoma, a cholangioma, chondroblastoma, chondroma, chondrosarcoma, chorioblastoma, choriocarcinoma, colon cancer, common acute lymphoblastic leukaemia, craniopharyngioma, cystocarcinoma, cystofibroma, cystoma, cytoma, ductal carcinoma in situ, ductal papilloma, dysgerminoma, encephaloma, endometrial carcinoma, endothelioma, ependymoma, epithelioma, erythroleukaemia, Ewing's sarcoma, extra nodal lymphoma, feline sarcoma, fibroadenoma, fibrosarcoma, follicular cancer of the thyroid, ganglioglioma, gastrinoma, glioblastoma multiforme, glioma, gonadoblastoma, haemangioblastoma, haemangioendothelioblastoma, haemangioendothelioma, haemangiopericytoma, haematolymphangioma, haemocytoblastoma, haemocytoma, hairy cell leukaemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angiofibroma, Kaposi sarcoma, kidney tumour, large cell lymphoma, leukemia, chronic leukemia, acute leukemia, lipoma, liver cancer, liver metastases, Lucke carcinoma, lymphadenoma, lymphangioma, lymphocytic leukaemia, lymphocytic lymphoma, lymphocytoma, lymphoedema, lymphoma, lung cancer, malignant mesothelioma, malignant teratoma, mastocytoma, medulloblastoma, melanoma, meningioma, mesothelioma, metastatic cancer, Morton's neuroma, multiple myeloma, myeloblastoma, myeloid leukemia, myelolipoma, myeloma, myoblastoma, myxoma, nasopharyngeal carcinoma, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteosarcoma, ovarian cancer, Paget's disease of the nipple, pancoast tumor, pancreatic cancer, phaeochromocytoma, pheochromocytoma, plasmacytoma, primary brain tumor, progonoma, prolactinoma, renal cell carcinoma, retinoblastoma, rhabdomyosarcoma, rhabdosarcoma, solid tumor, sarcoma, secondary tumor, seminoma, skin cancer, small cell carcinoma, squamous cell carcinoma, strawberry haemangioma, T-cell lymphoma, teratoma, testicular cancer, thymoma, trophoblastic tumor, tumourigenic, vestibular schwannoma, Wilm's tumor, or a combination thereof.

Blood vessel proliferative disorders refer to antiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration, as well as a pivotal role in cancer development. Other examples of blood vessel proliferation disorders include arthritis and ocular diseases such as diabetic retinopathy, restenosis, retinopathies and atherosclerosis.

Mesangial cell proliferative disorders refer to disorders brought about by abnormal proliferation of mesangial cells. Mesangial proliferative disorders include various human renal diseases such as glomerulonephritis, diabetic nephropathy, malignant nephrosclerosis, thrombic microangiopathy syndromes, transplant rejection and glomerulopathies. In this regards, PDGFR has been implicated in the maintenance of mesangial cell proliferation.

Metabolic disorders that are implicated with abnormal PTK activity include psoriasis, diabetes mellitus, wound healing, inflammation and neurodegenerative diseases. For example, EGFR has been indicated in corneal and dermal wound healing. Defects in the Insulin-R and IGF-1R receptor are indicated in type-II diabetes mellitus.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar.

The term "treating" as used herein refers to abrogating, inhibiting, slowing or reversing the progression of a disease, ameliorating clinical symptoms of a disease or preventing the appearance of clinical symptoms of a disease. The term "preventing" is defined herein as barring a subject from acquiring a disorder or diseases.

The term "administering" as used herein refers to a method of bringing a compound of the present invention and a target protein tyrosine kinase together in such a manner that the tyrphostin can affect the catalytic activity of the tyrosine kinase directly; i.e. by interacting with the kinase itself, or indirectly; i.e. by interacting with another molecule on which the catalytic activity of the enzyme is dependent. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The term "contacting" as used herein refers to bringing into contact the protein tyrosine kinase and the compounds defined herein, under in vivo conditions or in vitro conditions as defined above.

The term "therapeutically effective amount" refers to the amount of a compound being administered which relieves to some extent one or more of the symptoms of the disorder being treated. Therapeutic effective doses for any compounds represented by formulas 1-19 described herein can be estimated initially from cell culture and/or an animal model. A dose can be formulated in an animal model, and this dose can be used to more precisely determine useful doses in humans.

The term "effective inhibitory amount" refers to the amount of a compound being administered that inhibits to some extent the protein tyrosine kinase with which it is contacted.

Pharmaceutical Compositions:

The present invention further provides pharmaceutical compositions comprising any of the compounds represented by the structure of formulas 1-19, and a pharmaceutically acceptable carrier or excipient.

As used herein, "pharmaceutical composition" means therapeutically effective amounts of the compounds of the present invention, together with suitable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or Lyophilized or otherwise dried formulations and include diluents of various buffer content (e.g., Tris-HCI, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Further comprehended by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially or intratumorally.

Moreover, as used herein "pharmaceutically acceptable carriers" are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see for example Saudek et al., *N. Engl. J. Med.* (1989), 321:574-579. In another embodiment, polymeric materials can be used. In yet another embodiment, a controlled release system can be placed in proximity to the therapeutic target, i.e., the brain, thus requiring only a fraction of the systemic dose (see, e.g., Goodson, *Medical Applications of Controlled Release*, supra (1984), 2:115-138. Preferably, a controlled release device is introduced into a subject in proximity to the site of inappropriate immune activation or a tumor. Other controlled release systems are discussed in the review by Langer, *Science* (1990), 249: 1527-1533).

The pharmaceutical preparation may comprise one or more of the compounds of formulas 1-19 alone, or may further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the selective androgen receptor modulator can be administered to a subject by, for example, subcutaneous implantation of a pellet; in a further embodiment, the pellet provides for controlled release of selective androgen receptor modulator over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tablet-forming processes. For oral administration, the selective androgen receptor modulators or their physiologically tolerated derivatives such as salts, esters, N-oxides, and the like are mixed with additives customary for this purpose, such as vehicles, stabilizers, or inert diluents, and converted by customary methods into a suitable form of administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, or with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the compounds of the present invention or their physiologically tolerated derivatives such as salts, hydrates and the like are converted into a solution, suspension, or emulsion, if desired with the substances customary and suitable for this purpose, for example, solubilizers or other auxiliaries. Examples are sterile liquids such as water and oils, with or without the addition of a surfactant, and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycols are preferred liquid carriers, particularly for injectable solutions.

The preparation of pharmaceutical compositions which contain an active component is well understood in the art. Typically, such compositions are prepared as aerosols of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof.

In addition, if desired, the composition can contain minor amounts of auxiliary substances such as wetting or emulsifying agents, pH buffering agents, which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the compounds of the present invention or their physiologically tolerated derivatives such as salts, hydrates, and the like are prepared and applied as solutions, suspensions, or emulsions in a physiologically acceptable diluent with or without a pharmaceutical carrier.

In another embodiment, the active compound can be delivered in a vesicle, in particular a liposome (see for example Langer, *Science* (1990), 249:1527-1533; Treat et al., *Liposomes in the Therapy of Infectious Disease and Cancer* (1989), Lopez-Berestein and Fidler (eds.), Liss, N.Y., 353-365.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Example 1

Synthesis

The general procedure for the synthesis of compounds 6-8, 11-13, and 15-17 is drawn schematically in FIG. 1, and disclosed hereinbelow:

General Procedure for the Synthesis of the Following Intermediate Compounds: Denoted (i) Wherein Y=H, (ii) Wherein Y=OMe and (iii) Wherein Y=Br:

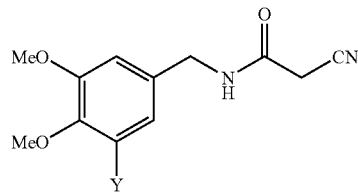

An amine (1.2 equiv) and methyl cyanoacetate (1 equiv) were stirred at room temperature until the precipitation of the product was observed. The product was collected by filtration, washed twice with ethanol, and dried under reduced pressure. The product was obtained as a white solid in 70-80% yield.

For compound (i): $^1$H NMR (300 MHz, in CDCl$_3$): δ 6.85 (m, 3H), 6.3 (bs, 1H), 4.41 (d, J=6.0 Hz, 2H), 3.89 (s, 3H), 3.87 (s, 3H), 3.40 (s, 2H). MS (ESI). found (m/z) 235.67; calculated [please confirm] for C$_{12}$H$_{14}$N$_2$O$_3$ (MH$^+$) 235.25.

For compound (II): $^1$H NMR (300 MHz, in CDCl$_3$): δ 6.49 (s, 2H), 6.37 (bs, 1H), 4.40 (d, J=4.4 Hz, 2H), 3.86 (s, 6H), 3.84 (s, 3H), 3.43 (s, 2H). MS (ESI). found (m/z) 265.60; calculated for C$_{13}$H$_{17}$N$_2$O$_4$ (MH$^+$) 265.11.

For compound (iii): $^1$H NMR (300 MHz, in CDCl$_3$): δ 7.04 (s, 1H), 6.79 (s, 1H), 4.39 (d, J=6.0 Hz, 2H), 3.89 (s, 3H), 3.87 (s, 3H), 3.45 (s, 2H).

General procedure for the synthesis of the following intermediate compounds denoted (iv) wherein Y=H, (v) wherein Y=OMe and (vi) wherein Y=Br:

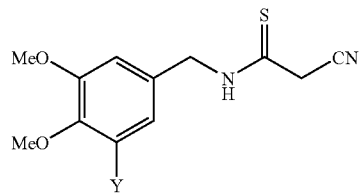

An amide (1 equiv) and Lawesson's reagent (0.55 equiv) were heated in dry toluene (ca. 2 mL/mmol of compounds (i-iii)) under reflux for 3 hours (until TLC indicated the disappearance of the amide). The reaction mixture was cooled and evaporated under reduced pressure. The residue was purified by flash chromatography to yield a pale yellow solid in 50-60% yield.

For compound (iv): $^1$H NMR (400 MHz, in CDCl$_3$+Acetone-d$_6$): δ 9.20 (bs, 1H), 6.84 (m, 2H), 6.78 (d, J=8 Hz, 1H) 4.71 (d, J=5.1 Hz, 2H), 3.89 (s, 2H), 3.81 (s, 3H), 3.80 (s, 3H). MS (CI). found (m/z) 251.43; calculated for C$_{12}$H$_{14}$N$_2$O$_2$S (MH$^+$) 250.32.

For compound (v): $^1$H NMR (300 MHz, in Acetone-d$_6$): δ 9.20 (bs, 1H), 6.72 (s, 2H), 4.77 (d, J=5.2 Hz, 2H), 4.06 (s, 2H), 3.80 (s, 6H), 3.71 (s, 3H). MS (CI). found (m/z) 281.51; calculated for C$_{13}$H$_{17}$N$_2$O$_3$S (MH$^+$) 281.34.

For compound (vi): $^1$H NMR (400 MHz, in CDCl$_3$): δ 7.08 (s, 1H), 6.82 (s, 1H), 4.78 (d, J=5.2 Hz, 2H), 3.98 (s, 2H), 3.88 (s, 3H), 3.87 (s, 3H). General procedure for the synthesis of the following intermediate compounds denoted (vii) wherein X=Br and Y=H, (viii) wherein X=I and Y=H, (ix) wherein X=F and Y=OMe, (x) wherein X=Cl and Y=OMe, (xi) wherein X=Br and Y=OMe, (xii) wherein X=I and Y=OMe, (xiii) wherein X=CF₃ and Y=OMe, (xiv) wherein X=Br and Y=Br, and (xv) wherein X=OMe and Y=Br:

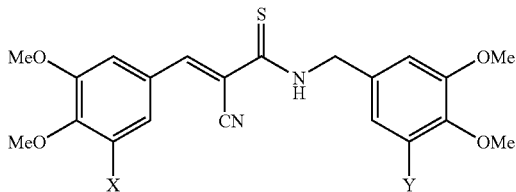

A catalytic amount of β-alanine (0.2 equiv) was added to a solution of β-cyanothioamide (1 equiv) and an aldehyde ((1.2 equiv) commercially available except for 3,4-dimethoxy-5-(trifluoromethyl)benzaldehyde which was prepared according to Backstrom et al., *J. Med. Chem.* (1989), 32:841-846) in ethanol (ca. 20 mL/mmol of compounds (iv-vi)). The solution was heated to 60° C. for 0.5 hour to overnight. The product was precipitated, collected by filtration, washed with H₂O, EtOH, and ether and then dried under reduced pressure to yield a pure yellow solid in 70% to quantitative yield.

For compound (vii): ¹H NMR (400 MHz, in CDCl₃): δ 8.69 (s, 1H), 7.95 (bt, 1H), 7.70 (d, J=2.0 Hz, 1H), 7.67 (d, J=2.0 Hz, 1H), 6.91 (m, 3H), 4.94 (d, J=5.0 Hz, 2H), 3.98 (s, 3H), 3.90 (s, 6H).

For compound (viii): ¹H NMR (400 MHz, in CDCl₃): δ 8.67 (s, 1H), 7.95 (bt, 1H), 7.86 (d, J=2.0 Hz, 1H), 7.72 (d, J=2.0 Hz, 1H), 6.92 (m, 3H), 4.94 (d, J=5.2 Hz, 2H), 3.98 (s, 3H), 3.90 (s, 6H).

For compound (ix): ¹H NMR (400 MHz, in Acetone-d₆): δ 9.60 (bs, 1H), 8.24 (s, 1H), 7.55 (m, 3H), 6.81 (s, 1H), 4.98 (s, 2H), 3.96 (s, 3H), 3.83 (s, 6H), 3.73 (s, 3H).

For compound (x): ¹H NMR (400 MHz, in CDCl₃): δ 8.69 (s, 1H), 7.99 (bt, 1H), 7.58 (d, J=2.0 Hz, 1H), 7.55 (d, J=2.0 Hz, 1H), 6.60 (s, 1H), 4.92 (d, J=5.2 Hz, 2H), 3.96 (s, 3H), 3.87 (s, 6H), 3.84 (s, 3H).

For compound (xi): ¹H NMR (300 MHz, in Acetone-d₆): δ 9.62 (bt, 1H), 8.21 (s, 1H), 7.81 (s, 1H), 7.76 (s, 1H), 6.79 (s, 2H), 4.96 (m, 2H), 3.94 (s, 3H), 3.81 (s, 6H), 3.71 (s, 3H). MS (CI). found (m/z) 494.73; calculated for C₂₁H₂₂BrN₂O₅S (MH⁺) 494.37.

For compound (xii): ¹H NMR (400 MHz, in CDCl₃): δ 8.66 (s, 1H), 7.99 (bt, 1H), 7.86 (d, J=2.0 Hz, 1H), 7.72 (d, J=2.0 Hz, 1H), 6.60 (s, 2H), 4.93 (d, J=5.0 Hz, 2H), 3.97 (s, 3H), 3.88 (s, 6H), 3.86 (s, 3H). MS (CI). found (m/z) 540.67; calculated for C₂₁H₂₁IN₂O₅S (M⁺) 540.37.

For compound (xiii): ¹H NMR (200 MHz, in CDCl₃): 8.75 (s, 1H), δ 8.22 (bt, 1H), 7.91 (d, J=2.0 Hz, 1H), 7.69 (d, J=2.0 Hz, 1H), 6.61 (s, 2H), 4.94 (d, J=5.0 Hz, 2H), 4.03 (s, 3H), 3.88 (s, 6H), 3.86 (s, 3H).

For compound (xiv): ¹H NMR (400 MHz, in Acetone-d₆+CDCl₃): δ 9.30 (bt, 1H), 8.43 (s, 1H), 7.72 (d, J=2.0 Hz, 1H), 7.17 (d, J=2.0 Hz, 1H), 7.07 (d, J=2.0 Hz, 1H), 5.01 (d, J=4.4 Hz, 2H), 3.95 (s, 3H), 3.87 (s, 3H), 3.81 (s, 3H).

For compound (xv): ¹H NMR (400 MHz, in CDCl₃): δ 8.74 (s, 1H), 8.00 (bt, 1H), 7.34 (s, 2H), 7.14 (s, 1H), 6.90 (s, 1H), 4.96 (d, J=4.5 Hz, 2H), 3.96 (s, 6H), 3.88 (s, 3H), 3.86 (s, 3H).

General Procedure for the Synthesis of Compounds 6-8, 11-13, 15-17:

Boron tribromide (1.5 equiv excess for each hydroxyl group) was added to a cold solution of the protected product in anhydrous CH₂Cl₂ (ca. 20 mL/mmol of compounds (vii-xv). The reaction mixture was allowed to warm to room temperature and stirred for 2-4 hours (until HPLC indicated the formation of the desired deprotected product). The solution was cooled and then treated with dilute hydrochloric acid. The solution was extracted three times with ethyl acetate, the organic layer was dried over Na₂SO₄, filtered and the solvent was evaporated. The crude product was recrystallized from water/ethanol to give yellow solid in 60-70% yield.

For compound 6: ¹H NMR (400 MHz, in Acetone-d₆): δ 9.45 (bs, 1H), 8.13 (s, 1H), 7.69 (d, J=2.1 Hz, 1H), 7.66 (d, J=2.1 Hz, 1H), 7.11 (d, J=2.0 Hz, 1H), 6.97 (d, J=2.0 Hz, 1H), 4.90 (d, J=5.4 Hz, 2H). MS (ESI). found (m/z) 498.73; calculated for C₁₇H₁₃Br₂N₂O₄S (MH⁺) 498.88.

For compound 7: ¹H NMR (300 MHz, in Acetone-d₆): 9.48 (bs, 1H), 8.08 (s, 1H), 7.66 (d, J=2.0 Hz, 1H), 7.63 (d, J=2.0 Hz, 1H), 6.46 (s, 2H), 4.79 (d, J=5.7 Hz, 2H). MS (ESI). found (m/z) 438.40; calculated for C₁₇H₁₄BrN₂O₅S (MH⁺) 438.26.

For compound 8: ¹H NMR (200 MHz, in Acetone-d₆): δ 9.42 (bs, 1H), 8.24 (s, 1H), 7.91 (d, J=2.1 Hz, 1H), 7.64 (d, J=2.1 Hz, 1H), 6.47 (s, 2H), 4.79 (d, J=5.5 Hz, 2H). MS (ESI). found (m/z) 484.80; calculated for C₁₇H₁₄IN₂O₅S (M⁺) 484.96.

For compound 11: ¹H NMR (300 MHz, in Acetone-d₆): δ 9.42 (bs, 1H), 8.08 (s, 1H), 7.61 (d, J=2.0 Hz, 1H), 7.49 (d, J=2.0 Hz, 1H), 6.47 (s, 2H), 4.80 (d, J=4.6 Hz, 2H). MS (ESI). found (m/z) 393.07; calculated for C₁₇H₁₄ClN₂O₅S (MH⁺) 393.81.

For compound 12: ¹H NMR (300 MHz, in Acetone-d₆): δ 9.47 (bs, 1H), 8.10 (s, 1H), 7.88 (d, J=2.0 Hz, 1H), 7.45 (d, J=2.0 Hz, 1H), 6.47 (s, 2H), 4.81 (d, J=5.4 Hz, 2H).

For compound 13: ¹H NMR (300 MHz, in Acetone-d₆): δ 9.47 (bs, 1H), 8.06 (s, 1H), 7.80 (d, J=2.1 Hz, 1H), 7.71 (d, H=2.1 Hz, 1H), 6.48 (s, 2H), 4.79 (d, J=5.4 Hz, 2H). MS (ESI). found (m/z) 427.33; calculated for C₁₈H₁₄F₃N₂O₅S (MH⁺) 427.37.

For compound 15: ¹H NMR (400 MHz, in Acetone-d₆): δ 9.40 (bs, 1H), 8.08 (s, 1H), 7.82 (d, J=2.0 Hz, 1H), 7.72 (d, J=2.0 Hz, 1H), 6.93 (m, 1H), 6.79 (m, 2H), 4.86 (d, J=5.4 Hz, 2H). MS (ESI). found (m/z) 422.80; calculated for C₁₇H₁₄BrN₂O₄S (MH⁺) 422.27.

For compound 16: ¹H NMR (300 MHz, in Acetone-d₆): δ 9.40 (bs, 1H), 8.13 (s, 1H), 7.82 (d, J=2.0 Hz, 1H), 7.68 (d, J=2.0 Hz, 1H), 6.93 (s, 1H), 6.78 (s, 2H), 4.86 (d, J=5.7 Hz, 2H). MS (ESI). found (m/z) 468.67; calculated for C₁₇H₁₃IN₂O₄S (M⁺) 468.27.

For compound 17: ¹H NMR (400 MHz, in Acetone-d₆): δ 9.45 (bs, 1H), 8.13 (s, 1H), 7.15 (s, 2H), 7.08 (d, J=2.0 Hz, 1H), 6.94 (d, H=2.0 Hz, 1H), 4.90 (d, J=5.0 Hz, 2H). MS (ESI). found (m/z) 437.67; calculated for C₁₇H₁₃BrN₂O₅S (M⁺) 437.26.

Figure 2:
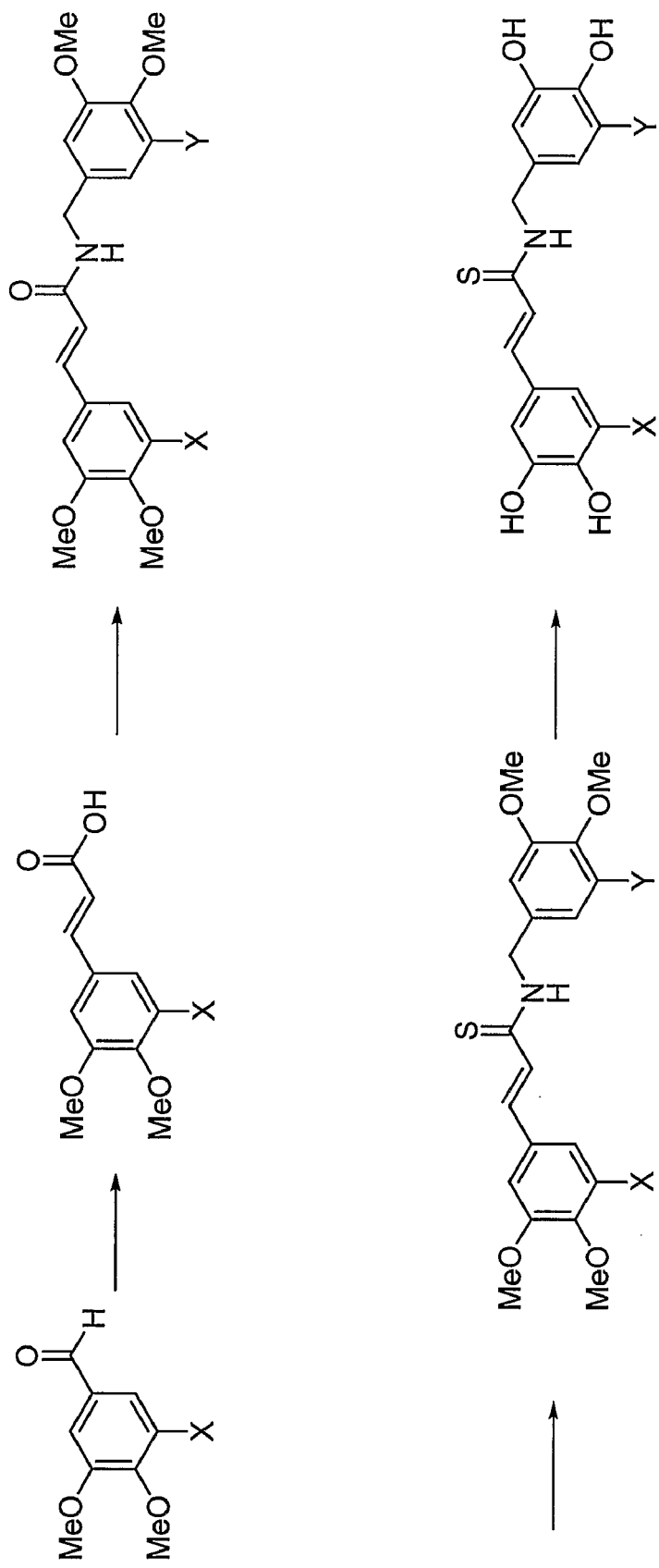
FIG. 2 Shows in schematic form a process for the synthesis of exemplary novel Tyrphostins of the invention. X and Y are independently selected from hydrogen, halogen, haloalkyl and $OR^8$ wherein $R^8$ is H, $C_1$-$C_4$ alkyl, acyl or a functional group that gives rise to hydroxyl upon hydrolysis.

The general procedure for the synthesis of compounds 5, 9-10,14 and 18 is drawn schematically in FIG. 2, and disclosed hereinbelow:

General Procedure for the Synthesis of the Following Intermediate Compounds Denoted (xvi) Wherein X=Br, (xvii) Wherein X=I, and (xviii) Wherein X=CF₃:

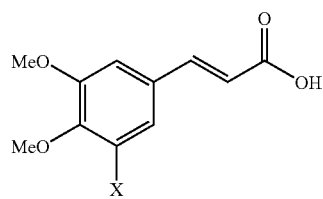

A catalytic amount of piperidine (0.2 equiv) was added to a solution of aldehyde ((1 equiv) commercially available except for 3,4-dimethoxy-5-(trifluoromethyl)benzaldehyde which was prepared according to Backstrom et al., *J. Med. Chem.* (1989), 32:841-846) and malonic acid (1.5 equiv) in pyridine. The reaction mixture was heated to 120° C. for 6 h. The solution was cooled to room temperature and concentrated HCl was added dropwise to pH<3. The white solid was collected by filtration, washed with water and dried under reduced pressure.

For compound (xvi): $^1$H NMR (300 MHz, in CDCl$_3$): δ 7.65 (d, J=15.9 Hz), 7.35 (d, J=2.1 Hz, 1H), 7.01 (d, J=2.1 Hz, 1H), 6.35 (d, J=15.9 Hz, 1H), 3.90 (s, 3H), 3.88 (s, 3H).

For compound (xvii): $^1$H NMR (400 MHz, in CDCl$_3$): δ 7.64 (d, J=2.0 Hz, 1H), 7.56 (d, J=2.0 Hz), 7.04 (d, J=2.0 Hz, 1H), 6.35 (d, J=16.0 Hz, 1H), 3.92 (s, 3H), 3.88 (s, 3H).

For compound (xviii): $^1$H NMR (400 MHz, in CDCl$_3$): δ 7.63 (d, J=16 Hz), δ 7.61 (s, 1H), 7.43 (s, 1H), 6.50 (d, J=16 Hz, 1H), 3.90 (s, 3H), 3.88 (s, 3H).

General Procedure for the Synthesis of the Following Intermediate Compounds Denoted (xix) Wherein X=Br and Y=Ome, (xx) Wherein X=I and Y=Ome, (xxi) Wherein X=CF$_3$ and Y=Ome and (xxii) Wherein X=Br and Y=Br:

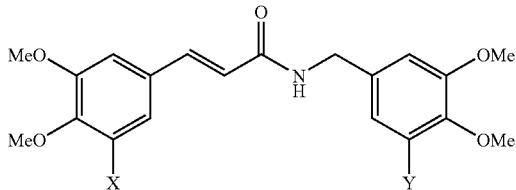

The solution of compounds (xvi-xviii, 1 equiv) in oxalyl chloride (4 equiv) was stirred for 1-2 hours at room temperature. The excess of oxalyl chloride was distilled off and the mixture was evaporated to dryness. The residue was dissolved in CH$_2$Cl$_2$ and added drop wise to a solution of an amine (0.85 equiv) and Et$_3$N (4 equiv) in CH$_2$Cl$_2$. the reaction mixture was stirred at room temperature for 0.5-1 hour (until TLC indicated the disappearance of the amine). The solvent was evaporated under reduced pressure and the residual oil was purified by flash chromatography.

For compound (xix): $^1$H NMR (300 MHz, in CDCl$_3$): δ 7.52 (d, J=15.8 Hz, 1H), 7.29 (s, 1H), 6.92 (s, 1H), 6.50 (s, 2H), 6.37 (d, J=15.8 Hz, 1H), 6.23 (bt, 1H), 4.46 (d, J=5.7 Hz, 2H), 3.81-3.85 (s, 15H). MS (BSI). found (m/z) 467.87; calculated for C$_{21}$H$_{25}$BrNO$_6$ (MH$^+$) 466.32.

For compound (xx): $^1$H NMR (400 MHz, in CDCl$_3$): δ 7.51 (d, J=2.0 Hz, 1H), 7.50 (d, J=15.6 Hz), 6.96 (d, J=2.0 Hz, 1H), 6.51 (s, 2H), 6.35 (d, J=15.6 Hz, 1H), 6.10 (bt, J=5.2 Hz, 1H), 4.47 (d, J=5.2 Hz, 2H), 3.85 (s, 3H), 3.84 (s, 3H) 3.82 (s, 6H), 3.81 (s, 3H).

For compound (xxi): $^1$H NMR (300 MHz, in CDCl$_3$): δ 7.52 (d, J=15.8 Hz, 1H), 7.29 (s, 1H), 6.92 (s, 1H), 6.50 (s, 2H), 6.37 (d, J=15.8 Hz, 1H), 6.23 (bt, 1H), 4.46 (d, J=5.7 Hz, 2H), 3.81-3.85 (s, 15H). MS (ESI). found (m/z) 467.87; calculated for C$_{21}$H$_{25}$BrNO$_6$ (MH$^+$) 466.32.

For compound (xxii): $^1$H NMR (400 MHz, in CDCl$_3$+ Acetone-d$_6$): 8.56 (bt, J=6.0 Hz, 1H), 7.39 (d, J=2.0 Hz, 1H), δ 7.38 (d, J=15.6 Hz, 1H), 7.28 (d, J=2.0 Hz, 1H), 7.09 (d, J=2.0 Hz, 1H), 7.05 (d, J=2.0 Hz, 1H), 6.68 (d, J=15.6 Hz, 1H), 4.32 (d, J=6.0 Hz, 2H), 3.85 (s, 3H), 3.80 (s, 3H), 3.74 (s, 3H), 3.67 (s, 3H). MS (ESI). found (m/z) 467.87; calculated for C$_{21}$H$_{25}$BrNO$_6$ (MH$^+$) 466.32.

General Procedure for the Synthesis of the Following Compounds Denoted 5 Wherein X=Br and Y=Ome, (xxiii) Wherein X=I and Y=Ome, (xxiv) Wherein X=CF$_3$ and Y=OMe, and (xxv) Wherein X=Br and Y=Br:

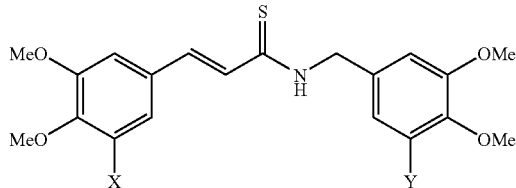

An amide (1 equiv) and Lawesson's reagent (0.55 equiv) were refluxed in toluene for 3 hours (until TLC indicated the disappearance of the amide). The reaction mixture was cooled and evaporated under reduced pressure. The residue was purified by flash chromatography to yield a pale yellow solid in 50-60% yield.

For compound 5: $^1$H NMR (300 MHz, in CDCl$_3$): δ 7.75 (d, J=15.3 Hz, 1H), 7.41 (d, J=2.1 Hz, 1H), 7.29 (d, J=2.1 Hz, 1H), 7.16 (d, J=15.3 Hz, 1H), 6.76 (s, 2H), 4.90 (m, 2H), 3.94 (s, 3H), 3.83 (s, 3H), 3.77 (s, 6H), 3.70 (s, 3H). MS (ESI). found (m/z) 483.87; calculated for C$_{21}$H$_{25}$BrNO$_5$S (MH$^+$) 483.38.

For compound (xxiii): $^1$H NMR (400 MHz, in CDCl$_3$): δ 7.71 (d, J=15.2 Hz, 1H), 7.6 (bt, 1H), 7.56 (d, J=1.8 Hz, 1H), 7.01 (d, J=1.8 Hz, 1H), 6.78 (d, J=15.2 Hz, 1H), 6.55 (s, 2H), 4.86 (d, J=5.0 Hz, 2H), 3.86 (s, 3H), 3.84 (s, 3H), 3.83 (s, 6H), 3.82 (s, 3H).

For compound (xxiv): $^1$H NMR (300 MHz, in CDCl$_3$): δ 7.75 (d, J=15.3 Hz, 1H), 7.41 (d, J=2.1 Hz, 1H), 7.29 (d, J=2.1 Hz, 1H), 7.16 (d, J=15.3 Hz, 1H), 6.76 (s, 2H), 4.90 (m, 2H), 3.94 (s, 3H), 3.83 (s, 3H), 3.77 (s, 6H), 3.70 (s, 3H). MS (ESI). found (m/z) 483.87; calculated for C$_{21}$H$_{25}$BrNO$_5$S (MH$^+$) 483.38.

For compound (xxv): $^1$H NMR (400 MHz, in CDCl$_3$): δ 7.74 (d, J=15.2 Hz, 1H), 7.52 (bt, 1H), 7.37 (d, J=1.9 Hz, 1H), 7.15 (d, J=1.9 Hz, 1H), 7.01 (d, J=1.9 Hz, 1H), 6.89 (d, J=1.9 Hz, 1H), 6.78 (d, J=15.2 Hz, 1H), 4.92 (d, J=5.3, 2H), 3.91 (s, 3H), 3.90 (s, 3H), 3.88 (s, 3H), 3.87 (s, 3H).

General Procedure for the Synthesis of Compounds 9-10, 14 and 18:

Boron tribromide (1.5 equiv excess for each hydroxyl group) was added to a cold solution of the protected product in anhydrous CH$_2$Cl$_2$ (ca. 20 mL/mmol of compounds 5 and (xxiii-xxv)). The reaction mixture was allowed to warm to room temperature and stirred for 2-4 hours (until HPLC indicated the formation of the desired deprotected product). The solution was cooled and then treated with dilute hydrochloric acid. The solution was extracted three times with ethyl acetate and the combined organic layer was dried over Na$_2$SO$_4$ and evaporated under reduced pressure. The crude product was recrystallized from water/ethanol to give the desired product in 60-70% yield.

For compound 9: $^1$H NMR (400 MHz, in Acetone-d$_6$): δ 9.16 (bs, 1H), 7.69 (d, J=15.4 Hz, 1H), 7.31 (d, J=1.9 Hz, 1H), 7.09 (d, J=1.9 Hz, 1H), 7.06 (d, J=15.4 Hz, 1H), 6.44 (s, 2H), 4.76 (d, J=5.7 Hz, 2H). MS (ESI). found (m/z) 411.93; calculated for C$_{16}$H$_{15}$BrNO$_5$S (MH$^+$) 411.97.

For compound 10: $^1$H NMR (400 MHz, in Acetone-d$_6$): δ 9.2 (bs, 1H), 7.67 (d, J=15.2 Hz, 1H), 7.51 (d, J=2.0 Hz, 1H), 7.12 (d, J=2.0 Hz, 1H), 7.02 (d, J=15.2 Hz, 1H), 6.44 (s, 2H), 4.76 (d, J=5.2 Hz, 2H). MS (ESI). found (m/z) 460.13; calculated for C$_{16}$H$_{15}$INO$_5$S (MH$^+$) 460.26.

For compound 14: $^1$H NMR (400 MHz, in Acetone-d$_6$): δ 9.16 (bd, 1H), 7.69 (d, J=15.4 Hz, 1H), 7.31 (d, J=1.9 Hz, 1H), 7.09 (d, J=1.9 Hz, 11H), 7.06 (d, J=15.4 Hz, 1H), 6.44 (s, 2H), 4.76 (d, J=5.7 Hz, 2H). MS (ESI). found (m/z) 411.93; calculated for $C_{16}H_{15}BrNO_5S$ ($MH^+$) 411.97.

For compound 18: $^1H$ NMR (300 MHz, in Acetone-$d_6$): δ 9.23 (bt, 1H), 7.68 (d, J=15.2 Hz, 1H), 7.31 (d, J=2.0 Hz, 1H), 7.09 (d, J=2.0 Hz, 1H), 7.09 (d, J=2.0 Hz, 1H), 6.99 (d, J=15.2 Hz, 1H), 6.91 (d, J=2.0 Hz, 1H), 4.85 (d, J=5.6 Hz, 2H). MS (ESI). found (m/z) 476.27; calculated for $C_{16}H_{14}Br_2NO_4S$ ($MH^+$) 476.15.

Figure 3:
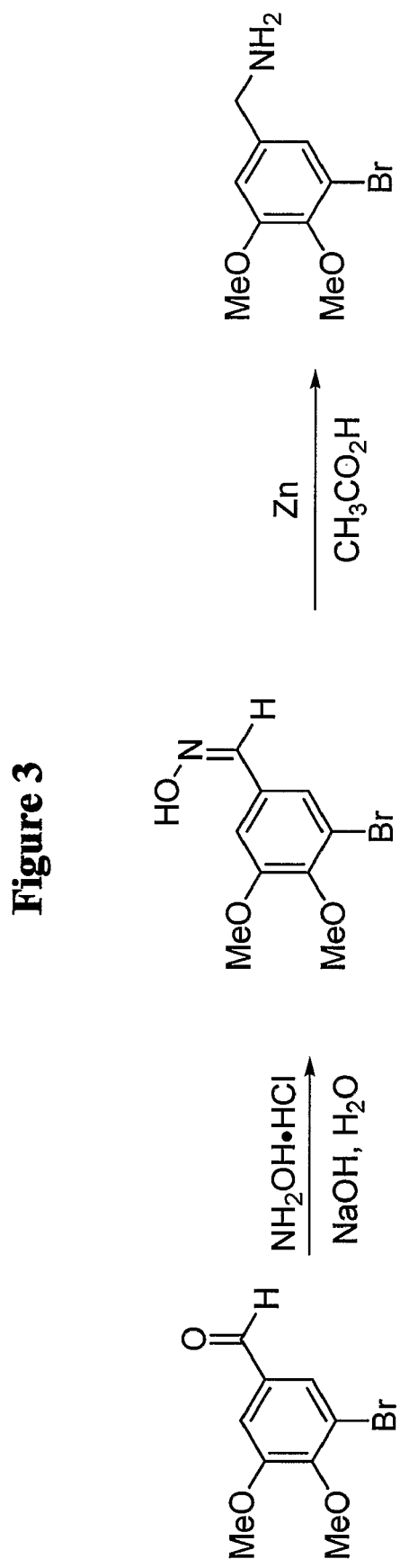
FIG. 3 Shows in schematic form a process for the synthesis of intermediates used in the synthesis of the novel Tyrphostins of the invention.

The general procedure for the synthesis of intermediates used in the synthesis of the novel tyrphostins of the present invention is shown in FIG. 3 and described hereinbelow:

General Procedure for the Synthesis of the Following Compound Denoted Herein (xxvi):

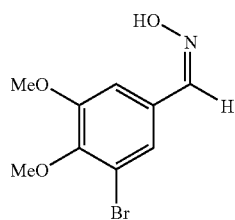

5-Bromoveratraldehyde (5.00 g, 20.5 mmol, 1 equiv) was dissolved in minimum amount of warm ethanol, and a solution of hydroxylamine hydrochloride (1.71 g, 24.6 mmol, 1.2 equiv) in water (30 mL) was added. Then aqueous solution of 10% sodium hydroxide (1.09 g, 27.3 mmol, 1.33 equiv) was added and the mixture was stirred at room temperature (until TLC indicated the disappearance of the aldehyde). After evaporation of the ethanol, the product was precipitated, collected by filtration, washed with water and dried under reduced pressure to yield a pure white solid in quantitative yield. $^1H$ NMR (300 MHz, in $CDCl_3$): δ 8.01 (s, 1H), 7.71 (s, 1H), 7.27 (d, J=1.8 Hz, 1H), 7.15 (d, J=1.8 Hz, 1H), 3.89 (s, 3H), 3.88 (s, 3H).

General Procedure for the Synthesis of the Following Compound Denoted Herein (xxvii):

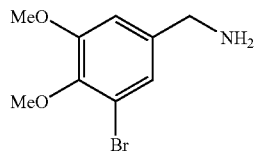

To a solution of (xxvi) (5.00 g, 19.2 mmol, 1 equiv) in 20 mL of acetic acid was added zinc (3.77 gr, 57.6 mmol, 3 equiv). The solution was refluxed until TLC showed the disappearance of the oxime. The zinc salts were filtered and washed with ethyl acetate. The filtrate was evaporated and aqueous sodium hydroxide was added. The aqueous layer was extracted three times with ethyl acetate. The organic layer was washed with brine, dried over $Na_2SO_4$ and evaporated under reduced pressure to yield yellowish oil in 55% yield. $^1H$ NMR (300 MHz, in $CDCl_3$): δ 7.09 (d, J=2.1 Hz, 1H), 6.85 (d, J=2.1 Hz, 1H), 3.90 (s, 3H), 3.86 (s, 3H), 3.82 (s, 2H).

Example 2

Biological Activity

Reagents and Antibodies

All chemicals used for chemical synthesis, namely bovine serum albumin, poly(Glu,Tyr) 4:1 (pGT), 2,2'-azido-bis-3-ethylbenzithiazoline-6-sulfonic acid, IGF1, methylene blue, 3-(4,5-dimethyl-2-thiazolyl)-2,5-diphenyl-2H-tetrazolium bromide (MTT), HRP-conjugated anti-phosphotyrosine PT-66 and diphosphorylated mitogen-activated protein kinase antibodies (PERK) were purchased from Sigma. Anti-phospho-IRS1 antibody was obtained from Oncogene Research Products, Germany; anti-IRS1 was obtained from Upstate Biotechnology, Inc. Anti-Akt1/2(PKB), anti-ERK2, and anti-IGF1Rβ antibodies were obtained from Santa Cruz Biotechnology. Anti-phospho(T308)Akt, anti-phospho (Ser636/Ser639)IRS1 and anti-PARP antibodies were obtained from Cell Signaling Technology. Dulbecco's modified Eagle's medium (DMEM) and fetal calf serum (FCS) were obtained from Biological Industries, Bet-Haemek, Israel. DMSO was obtained from BDH.

Inhibition of IGF1R-Catalyzed Substrate Phosphorylation

The general protein-tyrosine kinase substrate, poly(Glu, Tyr) 4:1 (pGT), was coated onto a 96-well Maxisorp plates (Nunc) by adding 125 µl of 0.1 mg/ml pGT in PBS to each well. Plates were sealed and incubated for 16 hours at 37° C., washed once with TBST (10 mM Tris-HCl, pH 7.5, 50 mM NaCl, and 0.1% Triton X-100) and once with DDW, dried for 2-3 hours, and stored at 4° C. The receptor was incubated (10 ng/well) in 20 µM ATP, 10 mM $MgCl_2$, 5 mM $MnAc_2$, and 20 mM Tris-HCl, pH 7.4, with or without inhibitors, for 20 min at 30° C. The plate was then washed with TBS with 0.2% Tween 20 (TBST) and blocked with 0.5% BSA in TBST. Mouse monoclonal anti-phosphotyrosine antibody, conjugated to Horse radish peroxidase (PT-66, 1:50000) was added to the plate. Following incubation for 45 min at room temperature, the plate was washed repeatedly with TBST. Detection was carried out with a color reagent, 2,2'-azido-bis-3-ethylbenzithiazoline-6-sulfonic acid, in citrate-phosphate buffer, pH 4.0, with 0.004% $H_2O_2$ for 10 min and monitored at 405 nm, all at room temperature. $IC_{50}$ values of inhibitors were calculated using the REGRESSION program. The assay was optimized with respect to the amount of IGF-1R (partially purified from cells overexpressing IGF1R), reaction time, and ATP concentration. The signal was linear for 30 min in the range of IGF1R protein concentrations up to 35 ng/well.

Inhibition of IGF1-Induced Signaling and Other Signaling Pathways (e.g. the EGF, PDGF and Insulin-Induced Signaling) in Intact Cells Tyrosine autophosphorylation of the β-subunit of IGF1R as well as downstream signaling induced by IGF1R were assayed in breast cancer MCF7 cells. Tyrosine autophosphorylation of the EGFR and the EGFR signaling was assayed in prostate cancer PC3 cells. Tyrosine autophosphorylation of the PDGFR and its signaling was assayed in fibroblasts overexpresing PDGFR. Tyrosine autophosphorylation of the IR and its signaling was assayed in fibroblasts overexpressing IR. Cells were seeded in 6-well plates (MCF7-250,000 cells/well, PC3-150,000 cells/well, fibroblasts-140,000 cells/well) and 24 hours later medium was replaced by serum-free medium (DMEM supplemented with 100 units/ml penicillin and 100 µg/ml streptomycin). Following 20 hours of serum-starvation medium was replaced with medium containing various concentrations of the inhibitors in 0.1% DMSO for additional 4 hours. Cells were then stimulated for 5 min with 50 ng/ml IGF-1 (MCF7 cells), 20 ng/ml EGF (PC3 cells), 50 ng/ml PDGF (fibroblasts overexpressing PDGFR) or 100 nM insulin (fibroblasts overexpressing IR), washed twice with PBS and lysed by boiling sample buffer (10% glycerol, 50 mM Tris-HCl, pH 6.8, 3% SDS, and 5%, β-mercaptoethanol). Equal amounts of protein per lane were separated by 8% SDS-PAGE and transferred to a nitrocellulose membrane (Sartorius AG). Phosphorylated proteins were immunoblotted with anti-phospho-IGF1R (phosphor-IGF1R), anti-phosphotyrosine-IRS1 (phospho-IRS1), anti-phospho(T308)Akt (phospho-PKB), anti-phospho-Erk (phospho-ERK), anti-phosphotyrosine 4G10&PY20 (pY-EGFR or pY-PDGFR), anti-phospho-Ser$^{636/639}$-IRS1 (pS$^{636/639}$-IRS1) and anti-phospho-STAT3 (phospho-STAT3) antibodies. Detection was performed with horseradish peroxidase-conjugated secondary antibody using the ECL system. Blots were then stripped of antibodies, blocked with TBST with 5% low fat milk and re-probed with antibodies detecting both the phosphorylated and the non-phosphorylated corresponding proteins e.g. IGF1Rβ, IRS1, PKB, ERK, IRβ, PDGFR and Stat3.

In addition, lysates were prepared from cells exposed to inhibitors at various concentrations for 24 hours in the presence or the absence of FCS without stimulation. Lysate preparation and western blot were the same as described above. Apoptosis was detected by immunoblotting with rabbit anti-PARP antibodies.

Proliferation Assay

Various cancer cell lines (listed in table 1) were plated at a density of 1000-5000 cells/well in 96-well plates in 90111 growth medium containing 10% FCS, 100 units/ml penicillin and 100 μg/ml streptomycin. Inhibitors were added a day later in 10 μl of 1% DMSO in DDW to obtain final concentrations of 0, 0.1, 0.3, 1, 3, and 10 μM. The final concentration of DMSO (0.1% DMSO) was kept constant in all samples. Medium with inhibitors was refreshed a day and two days later. Following exposure of the cells to the inhibitors for 72 hours at 37° C., the cells were fixed in 0.5% gluteraldehyde in medium for 10 min, washed three times with DDW, once with 0.1M sodium borate buffer pH 8.5 and stained with 1% methylene blue dissolved in 0.1M borate buffer solution for 60 min. Excess dye was washed out and cell-bound dye was eluted with 200 μl/well of 0.1 M HCl. The optical density value was read at 620 nm in ELISA plate reader. The data was analyzed in Microsoft Excel, using the vehicle control as 100% proliferation. The assays were performed in triplicates. The values in table 1 represent $IC_{50}$ values derived from the dose-dependent growth curves obtained.

Clonogenic Assay

Various cancer cells (listed in table 1) were seeded at a very low concentration (19 cells/well in 96-well plates or 63 cells/well in 24-well plates) in growth medium. A day later medium was replaced with growth medium containing various concentrations of inhibitors in a final concentration of 0.1% DMSO. The inhibitor-containing medium was refreshed three times a week. Following approximately two weeks cells were fixed by adding Gluteraldehide (0.5% final concentration) for 10 min, washed three time with DDW, once with borate buffer 0.1M and stained for 1 hour with 1% Methylene Blue in borate buffer 0.1M. Access stain was washed with water, and following drying colonies were counted. Alternatively, stain was extracted by 0.1N HCl for 1 hour and absorbance at 620 nm was measured by ELISA Reader. The assays were performed in triplicates. The values in table 1 represent $IC_{50}$ values derived from the dose-dependent growth curves obtained.

In-Vivo Effects on Prostate, Ovarian, Melanoma and Pancreatic Tumor Growth in Xenograft Models Human hormone-refractory prostate cancer PC3 cells (ATCC, $1.5 \times 10^6$ cells per mouse) were injected subcutaneously into the right leg of Nude:Hsd mice (purchased from Harlan). Ten days later, when palpable tumors had developed, mice were divided into 3 groups with similar average tumor size. The untreated group (UT) did not receive any treatment. The mice treated with compound 7 group were daily injected with compound 7 dissolved in the below described vehicle, and the vehicle-treated group (veh) was daily injected by the vehicle alone. Vehicle included 4.4% DMSO, 1.2% Ethanol and 50% PEG400 in DDW; Groups were composed of 3 mice per group. Dose administered IP was 50 mg/Kg (4 ml/Kg) once a day for one month. The length (l) and the width (w) of the tumors were measured every day and the volumes of the tumors were calculated as follows: $v=lw^2/2$. Graphs present average volumes of the tumors versus time in days. The procedure was followed for the other described in-vivo studies with the following modifications:

Human ovary cancer A2780 cells (from ECACC, $2 \times 10^6$ cells per mouse) were injected subcutaneously into the right leg of female Nude:Hsd mice (purchased from Harlan). Inhibitors were injected IP daily at doses of 20 mg/kg (Exp. 2&3) or 50 mg/kg (Exp. 4) dissolved in 4.4% DMSO, 0.12% EtOH, 50% PEG-400 in DDW at volume of 4 ml/kg. The Veh group received 4.4% DMSO, 0.12% EtOH, 50% PEG-400 in DDW at volume of 4 ml/kg.

The mouse B16 melanoma cells ($1.5 \times 10^6$ cells per mouse) were injected subcutaneously into the right leg of male Nude:Hsd mice (purchased from Harlan). Inhibitors were injected IP daily at a dose of 20 mg/kg dissolved in 4.4% % DMSO, 1.2% EtOH, 33% PEG-400 in DDW at volume of 4 ml/kg.

The human YUMAC metastatic melanoma cells ($2 \times 10^6$ cells per mouse), provided by Dr. Ruth Halaban (Yale University), were injected subcutaneously into the right leg of male Nude:Hsd mice (purchased from Harlan). Inhibitors were injected IP daily at a dose of 20 mg/kg dissolved in 8% EtOH, 2% Tween-80, 20% PEG-400 and 20% solutol in DDW at volume of 4 ml/kg.

Human pancreatic cancer Pancl cells ($2 \times 10^6$ cells per mouse) were injected subcutaneously into the right leg of male Nude:Hsd mice (purchased from Harlan). Compound 7 was injected intratumorally (IT) daily at doses of 125 μg/mouse in 0.06% DMSO and 2.16% PEG400 in saline.

In-vitro Inhibition of Keratinocyte Growth

Primary keratinocytes were seeded in 96-well plates in growth factor enriched medium. After 48 hours medium was refreshed and compound 7 was added at the indicated concentrations (0 is 0.1% DMSO which was kept constant in all wells). Every 24 hours medium and compound 7 were refreshed, and 5 days following seeding cells were fixed with 0.5% gluteraldehide for 10 min, stained with Methylene-Blue. Access stain was washed away and the bound stain was extracted by 0.1N HCl. Absorbance at 620 nm wavelength was read in ELISA reader.

Results

Biochemical Characterization of the Compounds of the Present Invention: Inhibition of IGF1R Activity in Cell-Free Assay As shown in table 1 and table 2, compounds 6-18 inhibited the kinase activity of partially purified IGF1R in a dose-dependent manner showing IC50 values of 30-200 nM. Elimination of the hydroxyl groups increases IC50 values, as demonstrated by the comparison of compound 19 and 7 (table 1). Kinetic studies show that compound 7, as well as compounds 6 and 8 do not compete with ATP, as elevation of the ATP concentrations does not induce an increase in the IC50 values determined in a cellular-free kinase assay of IGF1R (table 2).

TABLE 1

IC50 values of IGF1R activity in cellular free kinase assay

| Compound No. | $IC_{50}$ (nM) |
|---|---|
| 6 | 98 |
| 7 | 116 |
| 8 | 76 |
| 9 | 78 |
| 10 | 33 |
| 11 | ND |
| 12 | 169 |
| 13 | 68 |
| 15 | 115 |
| 16 | 193 |
| 17 | 49 |
| 18 | 196 |
| 19 | 700 |

TABLE 2

Kinetic studies testing the competition of the inhibitors with ATP in cellular free kinase assay of IGF1R

| | $IC_{50}$ nM | | |
|---|---|---|---|
| [ATP] μM | #7 | #8 | #6 |
| 2.5 | 190 | 190 | 74 |
| 5 | 163 | 110 | 56 |
| 10 | 124 | 100 | 92 |
| 20 | 90 | 80 | 55 |
| 50 | 80 | 100 | 98 |

Inhibition of IGF1R in Cells

Figure 4A:
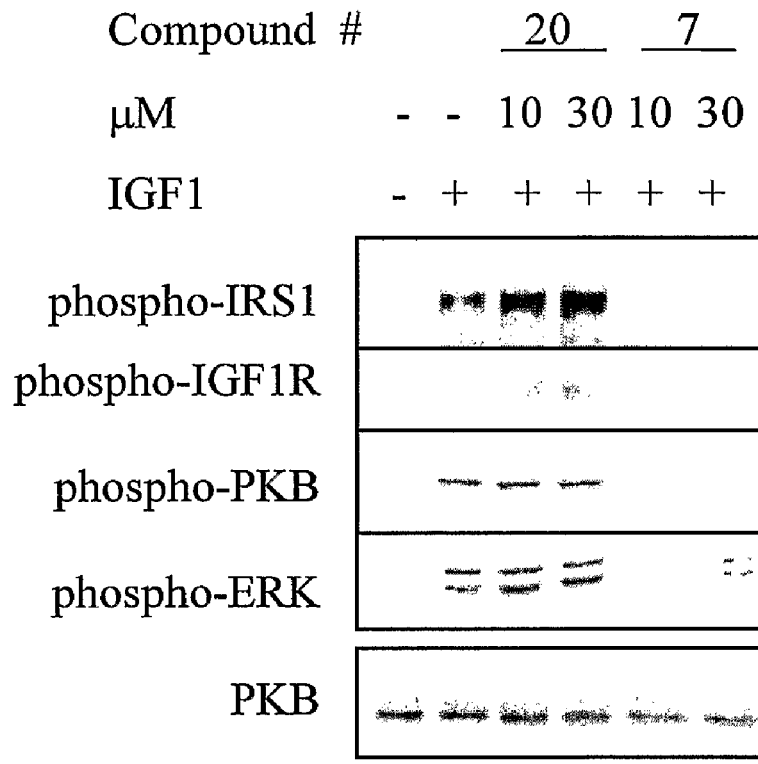
FIGS. 4A and 4B show that compound 7 induces inhibition of IGF1R and its signaling in intact cancer cells.

Exposure of breast cancer MCF7 cells to compound 7 yielded a significant inhibition of IGF1-induced signaling. FIG. 4A shows that while the control molecule 20 (see structure hereinbelow) had no effect on the signaling, compound 7 dramatically inhibited the autophosphorylation of IGF1R, the IGF1-induced tyrosine phosphorylation of IRS1 (a direct substrate of IGF1R) and the IGF1-induced activation of two main anti-apoptotic and proliferative pathways downstream IGF1R, the Akt/PKB and the MAPK/ERK pathways.

Compound 20

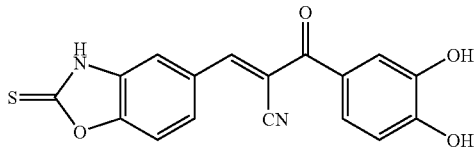

Figure 4B:
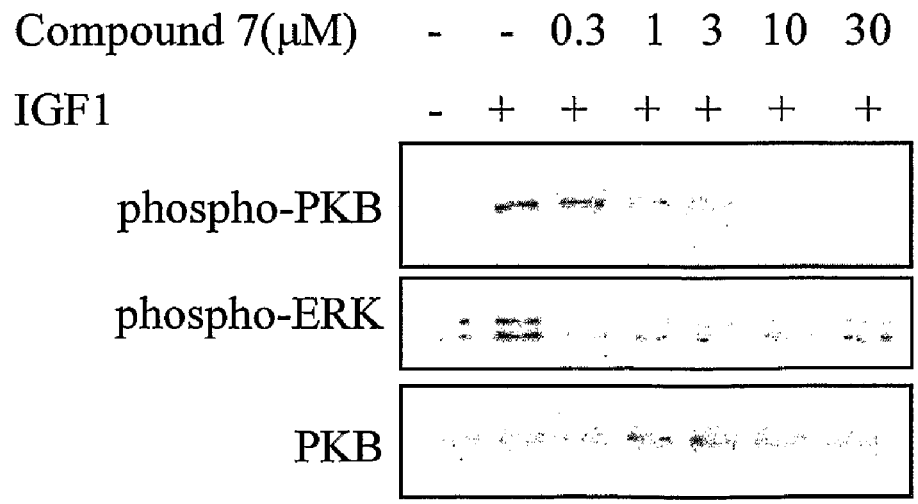

FIG. 4B exemplifies a dose-dependent activity of compound 7 in MCF7 cells, showing an IC50 value of 1-2 μM in inhibition of the central anti-apoptotic pathway downstream IGF1R, the Akt/PKB pathway. Inhibition of the MAPK/ERK pathway activation is detected at even lower concentrations.

Figure 5A:
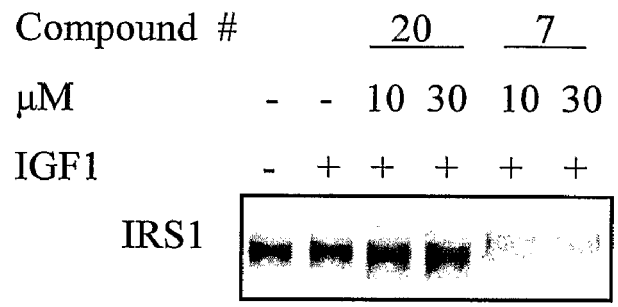
FIGS. 5A 5B and 5C show that compound 7 induces Serine-phosphorylation on IRS1 and a decrease in the cellular levels of IRS1 in breast cancer MCF7 cells.
Figure 5B:
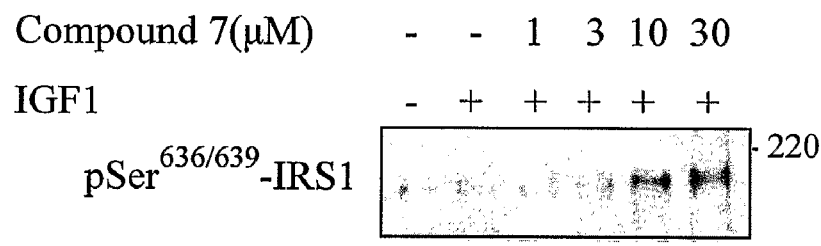

Compound 7 was unexpectedly found to induce a decrease in the cellular levels of IGF1R-direct substrate IRS1 in breast cancer MCF7 cells (FIG. 5). This effect was shown to be long-lasting (FIG. 5B). The decrease in IRS1 levels was detected even at 24 hours following exposure of the cells to compound 7, accompanied by inhibition of its downstream signaling pathway—the antiapoptotic PKB/Akt pathway and subsequent cleavage of PARP known as a marker for cell apoptosis.

Without wishing to be bound by any particular mechanism or theory, it is contemplated that the decrease in IRS1 levels induced by compound 7 is a result of the induction of a secondary negative regulation, in which IRS1 undergoes inhibitory phosphorylation on serine residues and subsequent degradation. This effect is believed to be of high importance in anti-cancer activity stemming from inhibitory mechanisms of PTK signal transduction. It is further contemplated that, Compound 7 as well as other compounds of the present invention which consist of trihydroxy benzyl thioamide and halogen or halomethyl moieties in the second catecholic ring, induce Ser-phosphorylation of IRS1 and/or a decrease in IRS1 levels. These structures show higher activity both in-vitro (inhibition of cancer cell proliferation) and in-vivo (inhibition of tumor growth), as compared to related molecules (eg. compound 6) which show no effect on IRS1 levels or Ser-phosphorylation in cells.

Figure 6:
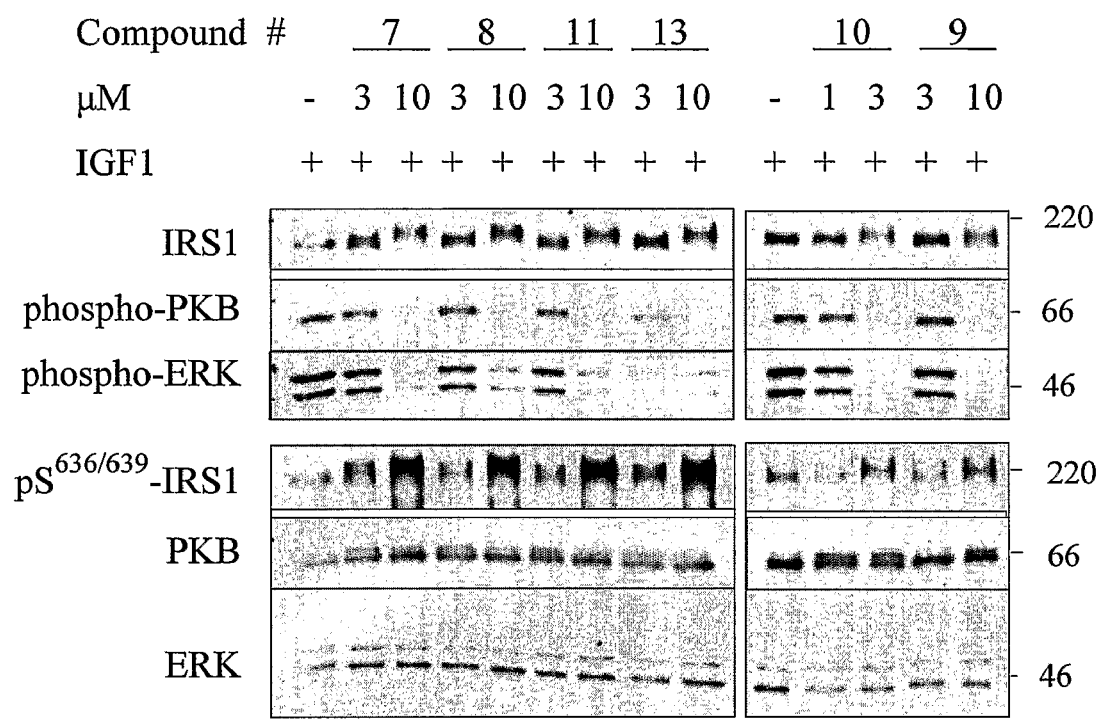
FIG. 6 shows Ser-phosphorylation on IRS1 following treatment of breast cancer MCF7 cells with compounds 7, 8, 9, 10, 11, and 13. Inhibition of the activation of IGF1R downstream signaling pathways, namely ERK and PKB are demonstrated as well.
Figure 7A:
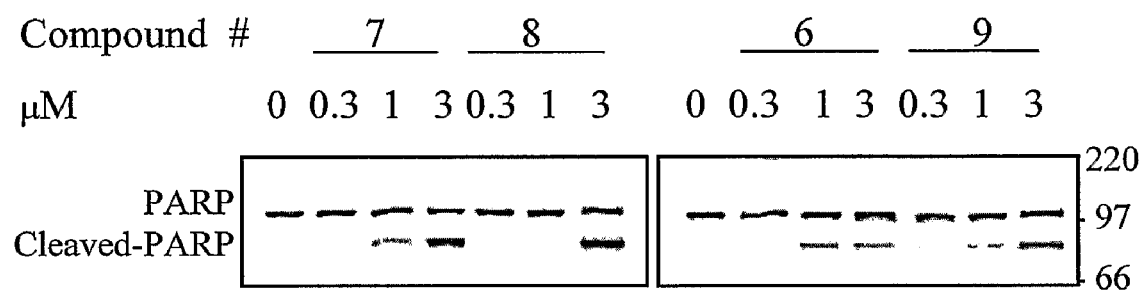
FIGS. 7A and 7B show treatment of ovarian cancer A2780 cells with compounds 7, 8 and 9 in comparison to compound 6.
Figure 7B:
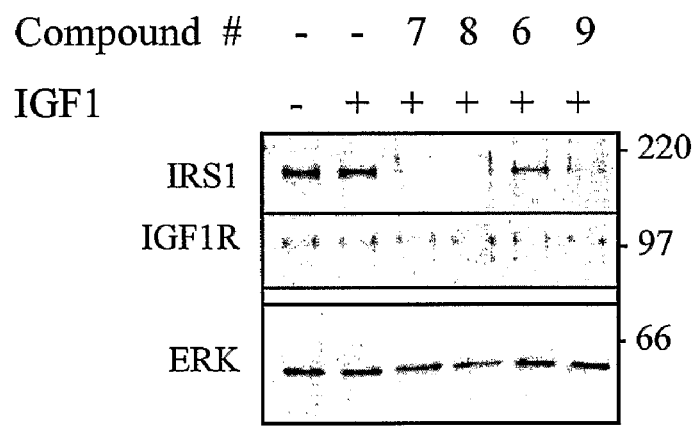
Figure 8:
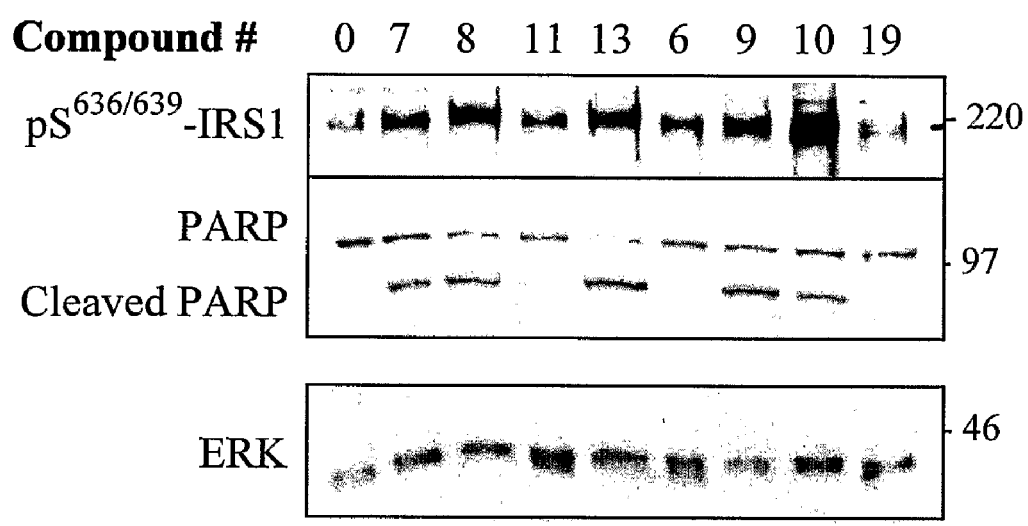
FIG. 8 shows that Ser-phosphorylation on IRS1 as well as cleavage of PARP (apoptosis) are detected in metastatic melanoma YUMAC cells treated with compounds 7, 8, 9, 10, and 13 in comparison to compounds 11 and 19.

The increase in IRS1 Ser-phosphorylation induced by the treatment of the cells with compound 7 is demonstrated by immunoblotting with specific antibodies against IRS1 phosphorylated on Ser residues 636 & 639 (FIG. 5B) and by the shift in the IRS1 bands in FIG. 5A. Ser-phosphorylation of IRS1 is known to induce decoupling of IRS1 from IGF1R, and thereby inhibit IGF1R signaling. It is further shown that other related inhibitors in this sub-family (e.g. compounds 8, 9, 10, 11 and 13) also trigger IRS1-ser phosphorylation in breast cancer MCF7 cells (FIG. 6) as well as in metastatic melanoma YUMAC cells (FIG. 8). In ovarian cancer, A2780 cells, compound 7 as well as compounds 8 and 9 induced Ser-phosphorylation (shift up of IRS1 band in SDS-PAGE) and a decrease in cellular IRS1 levels (FIG. 7). This long-term effect on IRS1 is accompanied by apoptosis of the cancer cells as demonstrated for the ovarian cancer cells following 21 hours of exposure (FIG. 7) and for the melanoma cells following 24 hours of exposure (FIG. 8; 3 μM) to the novel inhibitors.

Figure 9A:
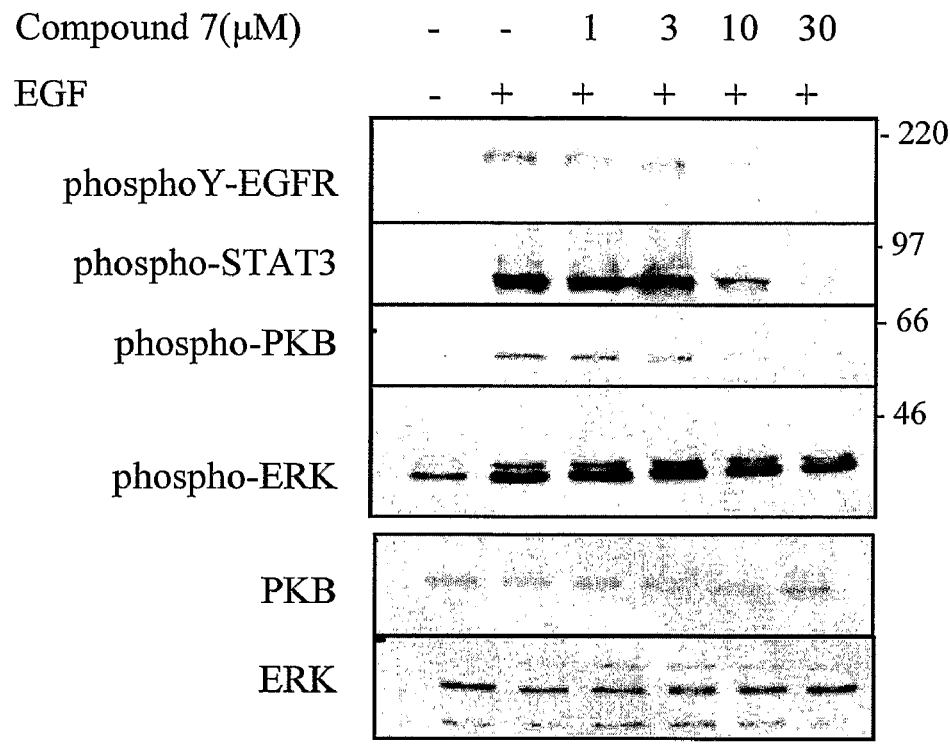
FIGS. 9A, 9B and 9C show that compound 7 inhibits the activation and downstream signaling of PDGFR, EGFR and IR tyrosine kinases in intact cells.
Figure 9B:
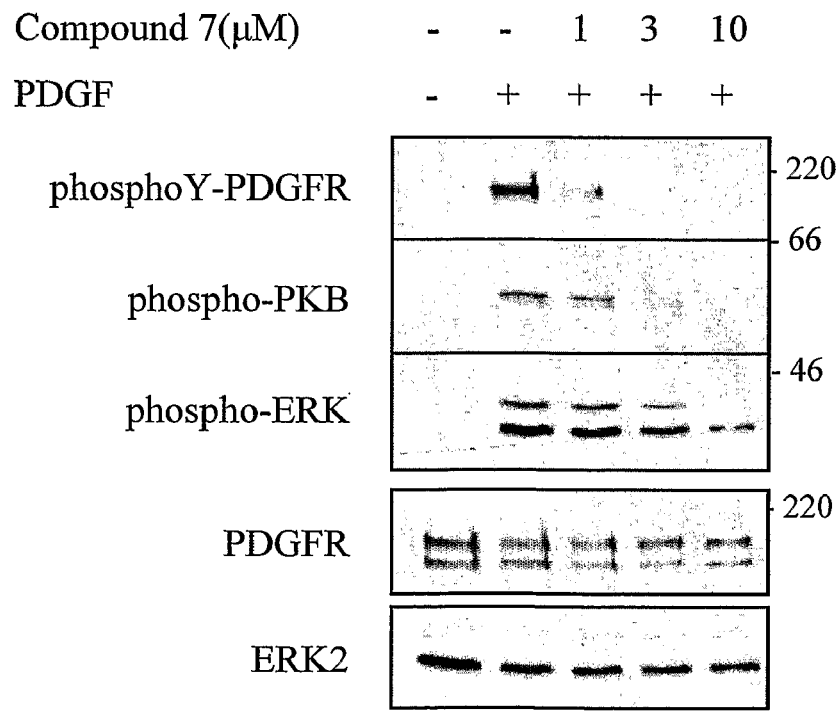
Figure 9C:
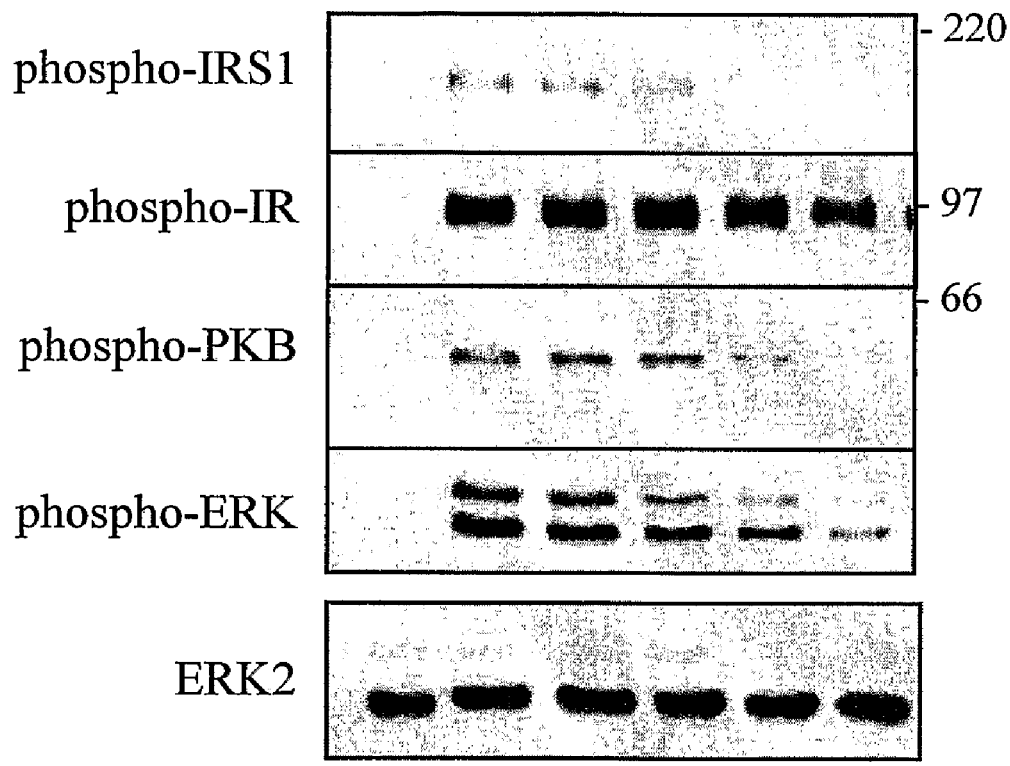

In addition to the inhibitory effects of compound 7 on IGF1R pathway, compound 7 inhibits other tyrosine kinases such as the EGFR, PDGFR and IR in intact cells (FIG. 9). These kinases have a central role in mitogenesis. Following incubation with compound 7, cells expressing these kinase receptors (e.g. prostate cancer PC3 cells expressing EGFR, fibroblast over-expressing PDGFR and fibroblasts over-expressing IR) were stimulated with either EGF, PDGF or insulin, FIGS. 9A, 9B and 9C respectively, and lysates were immunoblotted with anti-phosphotyrosine antibodies to detect autophosphorylation of the receptors. Downstream signaling of these receptors was measured as well.

Ser/Thr-kinases like MEK or PDK are not inhibited by compound 7 as detected by the phosphorylation levels of their substrates (ERK and PKB(Thr308) respectively) in cells where compound 7 had no inhibitory effect on upstream regulators.

Growth Inhibition

Compounds 6, 7, 8, and 9 were tested for their inhibitory potential in cell proliferation assay. In this assay cells were exposed to increasing concentrations of the molecules (at 0.1% DMSO in all wells) a day after seeding. Medium and inhibitors were refreshed every day, and following three days of treatment, cells were fixed and stained with methylene-Blue. IC50 values were determined from the curves of the optical density against compound concentration. The assay was performed in triplicates.

Figure 5C:
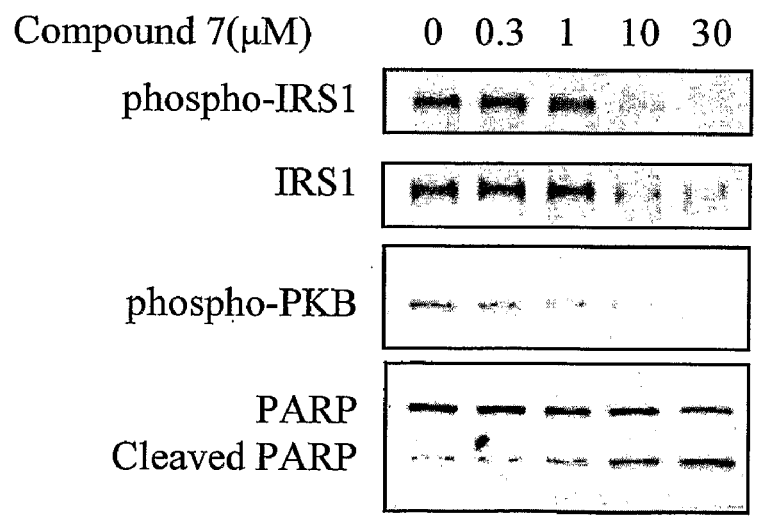

A panel of cancer cell lines from various indications was tested for its sensitivity to the molecules (table 3). Compounds 7, 8 and 9 showed anti-cancer activity while compound 6 had lower activity. The activity correlated to the ability of these molecules to induce Ser-phosphorylation & reduction of IRS1 levels in cells. As opposed to compound 6 (FIGS. 19A&B), compounds 7, 8, and 9 induce an increase in IRS1-ser-phosphorylation (FIGS. 5-8) and a decrease in IRS1 levels (FIGS. 5 and 7). 24 hours treatment triggers apoptosis of these cells as detected by the cleavage of PARP (FIGS. 5C, 7A and 8).

TABLE 3

The inhibitory activity ($IC_{50}$ values in μM) of compounds 6,7,8 and 9 in cell proliferation and in clonogenic assays of various cancer cell lines. Assays performed in triplicates.

| Indication | Cell line | Clonogenic assay IC50 (μM) | | | | Proliferation assay IC50 (μM) | | | |
|---|---|---|---|---|---|---|---|---|---|
| | | #6 | #7 | #8 | #9 | #6 | #7 | #8 | #9 |
| Prostate | PC3 | 0.7 | 4.2 | 1.0 | 1.2 | >10 | 2.8 | 4.6 | 2.7 |
| | | | | | | >10 | 3.9 | 3.6 | 2.0 |
| | DU145 | | | | | >10 | 6.6 | 6.5 | 1.8 |
| | LNCaP | | | | | >10 | >10 | 7.7 | 4.7 |
| | PC3-MM2 | | | | | >10 | 2.6 | 2.1 | 6.9 |
| Ovarian | A2780 | 0.1 | 0.4 | 0.4 | 0.3 | 6.8 | 0.6 | 0.6 | 0.4 |
| | OVCAR3 | | | | | >10 | 2.0 | 1.9 | 0.9 |
| | SKOV-3 | | | | | >10 | 5.3 | 3.5 | 4.3 |
| Colon | Colo-205 | | | | | >10 | 5.4 | 2.5 | 1.7 |
| | LIM 1215 | | | | | >10 | 6.5 | 6.4 | 3.3 |
| | LIM 1899 | | | | | >10 | 7.6 | 7.1 | 2.0 |
| | HT29 | 9.5 | 2.8 | 5.6 | 1.6 | >10 | 6.8 | 6.1 | 1.5 |
| Lung | QG56 | 2.4 | 1.7 | 1.4 | 0.5 | >10 | 5.2 | 4.4 | 2.0 |
| | NCI-H1975 | | | | | >10 | 2.5 | 2.3 | 2.7 |
| | PC-10 | | | | | >10 | 5.2 | 5.8 | 3.8 |
| | NCI-H526 | | | | | >10 | >10 | >10 | >10 |
| Glioma | U138MG | 2.2 | 1.8 | 1.6 | 0.5 | 2.0 | 0.8 | 0.8 | 0.2 |
| | U87MG | | | | | >10 | 6.9 | 2.4 | 6.6 |
| | MO59K | | | | | 6.8 | 0.7 | 0.9 | 1.4 |
| | MO59J | | | | | 8.3 | 2.1 | 1.6 | 0.9 |
| Breast | MDA MB 468 | | | | | >10 | >10 | 5.8 | 7.2 |
| | MDA MB 231 | | | | | >10 | 6.3 | 7.4 | >10 |
| | MDA MB 435 | | | | | >10 | 2.7 | 2.1 | 1.5 |
| | SKBR-3 | | | | | >10 | 9.9 | 9.0 | 6.0 |
| | MCF-7 | | | | | 2.1 | 4.8 | 2.8 | 2.5 |
| | T47D | | | | | >10 | 2.1 | 2.5 | 1.6 |
| Melanoma | B16 | 0.8 | 0.4 | 0.4 | | 7.9 | 1.9 | 1.7 | 1.4 |
| | YUMAC | | | | | 8.5 | 1.2 | 1.2 | 0.6 |
| | YURIF | | | | | >10 | 1.4 | 1.6 | 0.7 |
| Bladder | T24P | | | | | >10 | 1.2 | 0.9 | 1.4 |
| | 1376 | | | | | 2.5 | 0.9 | 0.8 | 1.4 |
| Pancreatic | PANC1 | | | | | >10 | >10 | >10 | >10 |
| | AsPC1 | | | | | >10 | >10 | 9.5 | >10 |
| Pro B | BAF3 Bcr-Abl | | | | | 7.7 | 8.2 | >10 | 6.1 |
| Leukemia | K562 | | | | | >10 | ~10 | ~10 | >10 |
| Myeloma | U266 | | | | | 9.8 | 0.8 | 0.8 | 0.9 |

The sensitivity of the human metastatic melanoma cells was tested against a wider set of compounds (table 4), and showed high sensitivity towards the molecules that induce IRS1 Ser-phosphorylation, e.g. compounds 7, 8, 9, 10 and 13 (FIGS. 6 & 8) as opposed to compounds 6, 17 and 19.

TABLE 4

Inhibition of human metastatic melanoma cells by a series of novel molecules.

| YUMAC | | YURIF | |
|---|---|---|---|
| Compound | IC50 (μM) | Compound | IC50 (μM) |
| 6 | 8.5 | 6 | >10 |
| 7 | 1.2 | 7 | 1.4 |
| 8 | 1.2 | 8 | 1.6 |
| 9 | 0.6 | 9 | 0.65 |
| 10 | 0.3 | 10 | 0.47 |
| 11 | 1.2 | 11 | 1.2 |
| 13 | 1 | 13 | 0.87 |
| 17 | >10 | 17 | >>10 |
| 19 | ~10 | 19 | >10 |

Results are presented in $IC_{50}$ values following 72 hours incubation of the cells with the molecules.

In-vivo Studies

Figure 10:
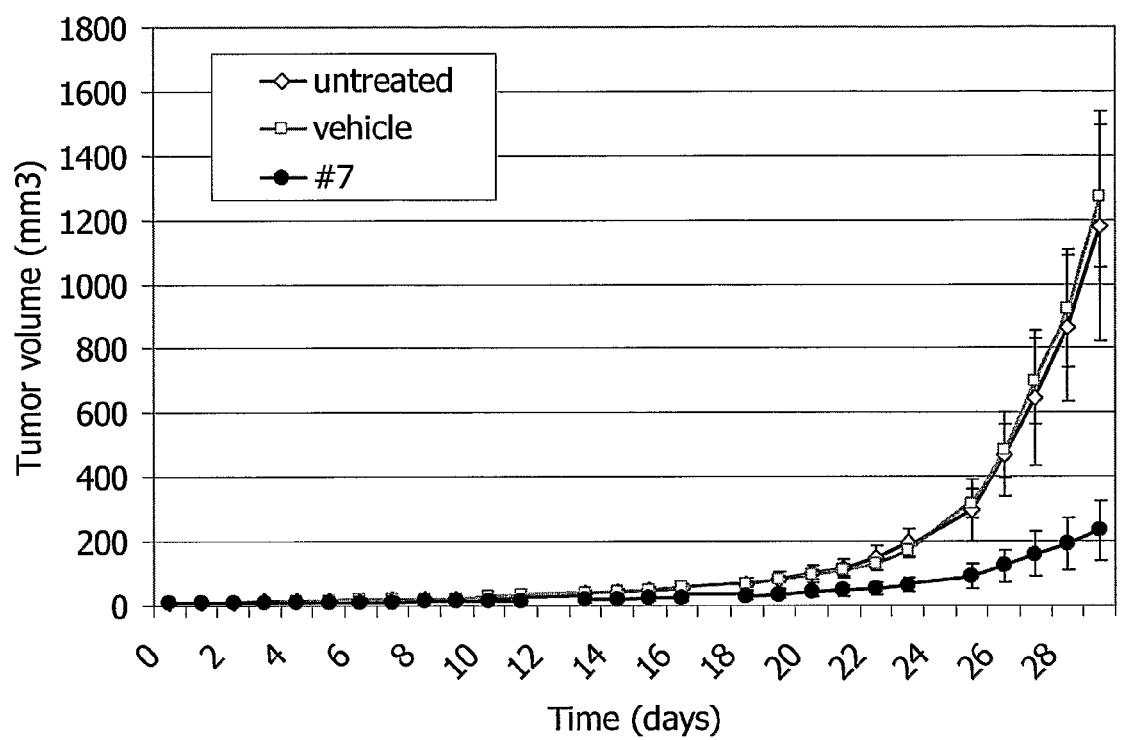
FIG. 10 shows that treatment of nude mice with compound 7 (IP, 1/day, 50 mg/kg) resulted in 82% growth inhibition of hormone-refractory prostate cancer (HRPC) PC3 tumors.
Figure 11:
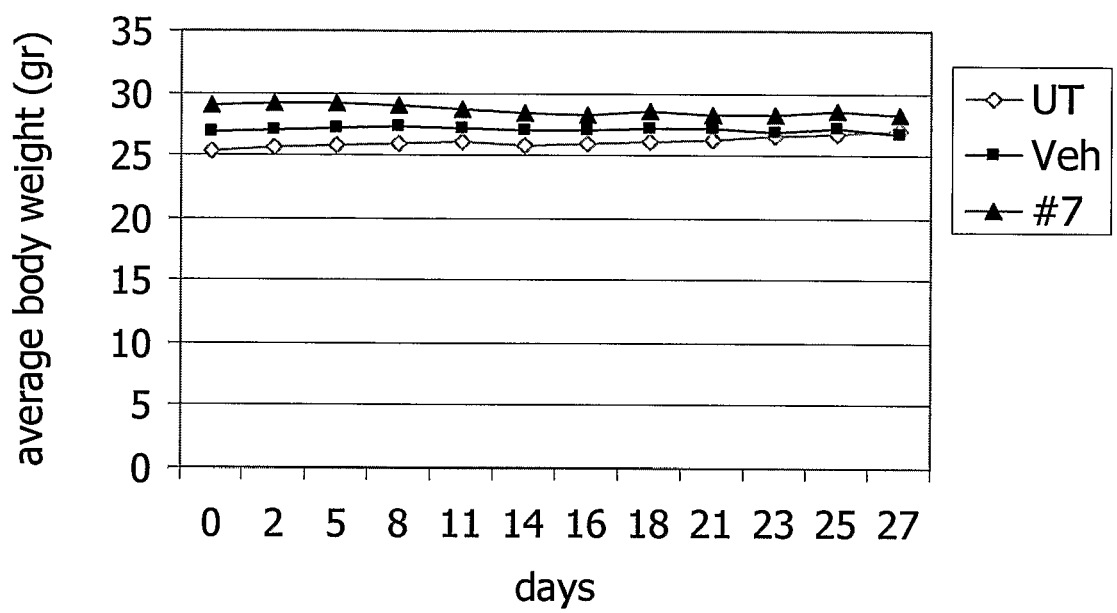
FIG. 11 shows that treatment of nude mice with compound 7 (IP, 1/day, 50 mg/kg) had no significant effect on body weight of the mice over 4 weeks (UT=untreated, Veh=vehicle).
Figure 16:
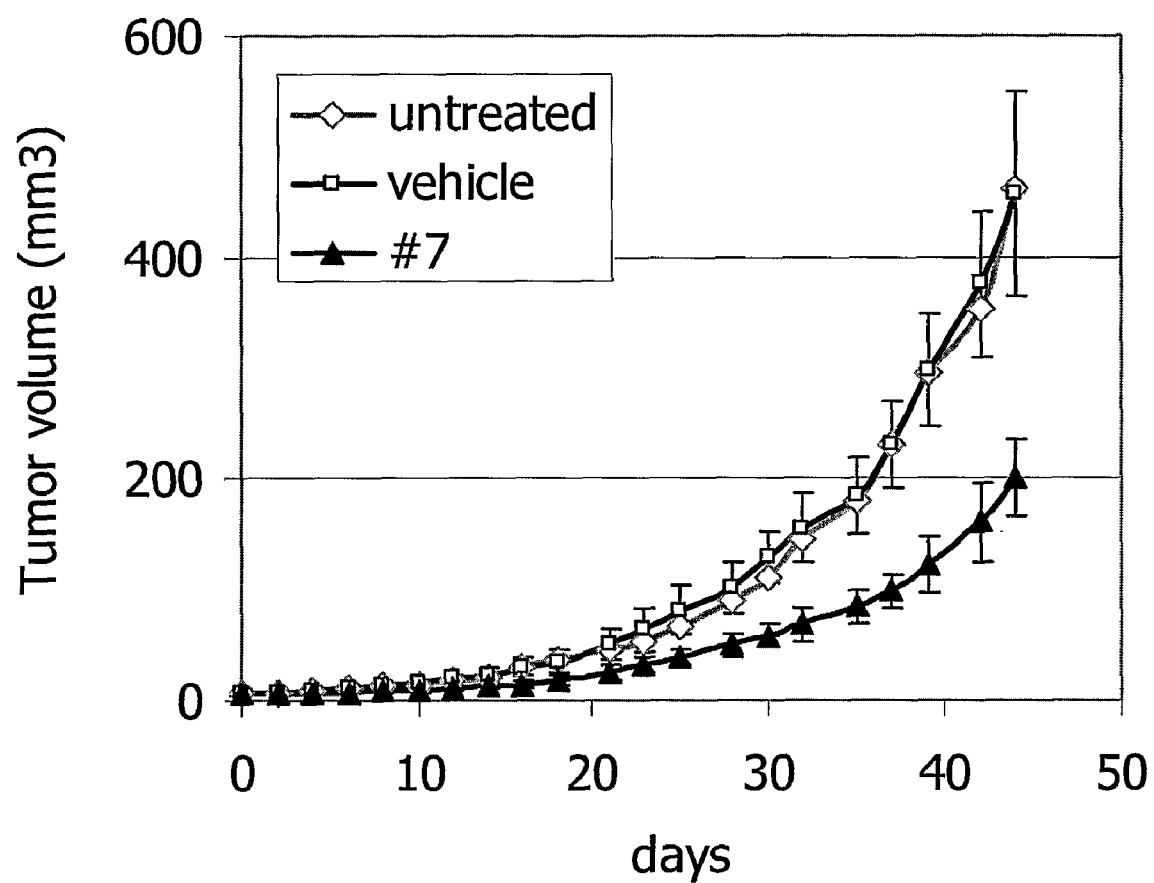
FIG. 16 shows that treatment of nude mice with compound 7 (intratumoral, 1/day, 125 µg/day) resulted in 50% growth inhibition of pancreatic cancer Panc1 tumors.

Compound 7 was tested for its inhibitory effect on tumor growth in animal model. Nude mice were subcutaneously injected with cancer cells in the flank of the mouse, and when tumors were measurable, administration of various compounds of the present invention started. Tumor dimensions presented in the graphs are those measured following the first administration. The model of human hormone-refractory prostate cancer (HRPC)PC3 was the first to be examined. FIG. 10 shows that systemic administration (IP) of compound 7 at dosage of 50 mg/kg once a day, resulted in inhibition of the tumor growth by 82% as compared to controls (vehicle treated and untreated). Furthermore, no significant effect on body weight of the nude mice was detected following one month of administration (FIG. 11). Additionally, Compound 7 was found efficient when tested using intratumoral administration on both HRPC and pancreatic PANC1 models (FIG. 16).

Figure 12:
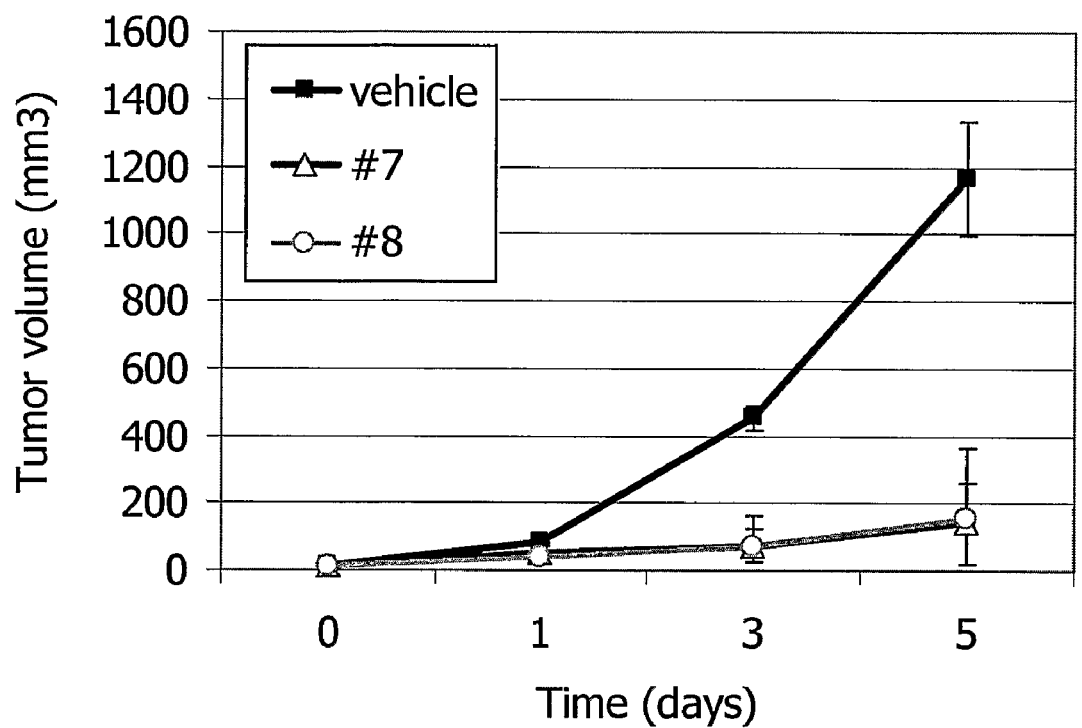
FIG. 12 shows that treatment of nude mice with compounds 7 or 8 (IP, 1/day, 20 mg/kg) resulted in 87% growth inhibition of ovarian cancer A2780 tumors.
Figure 13:
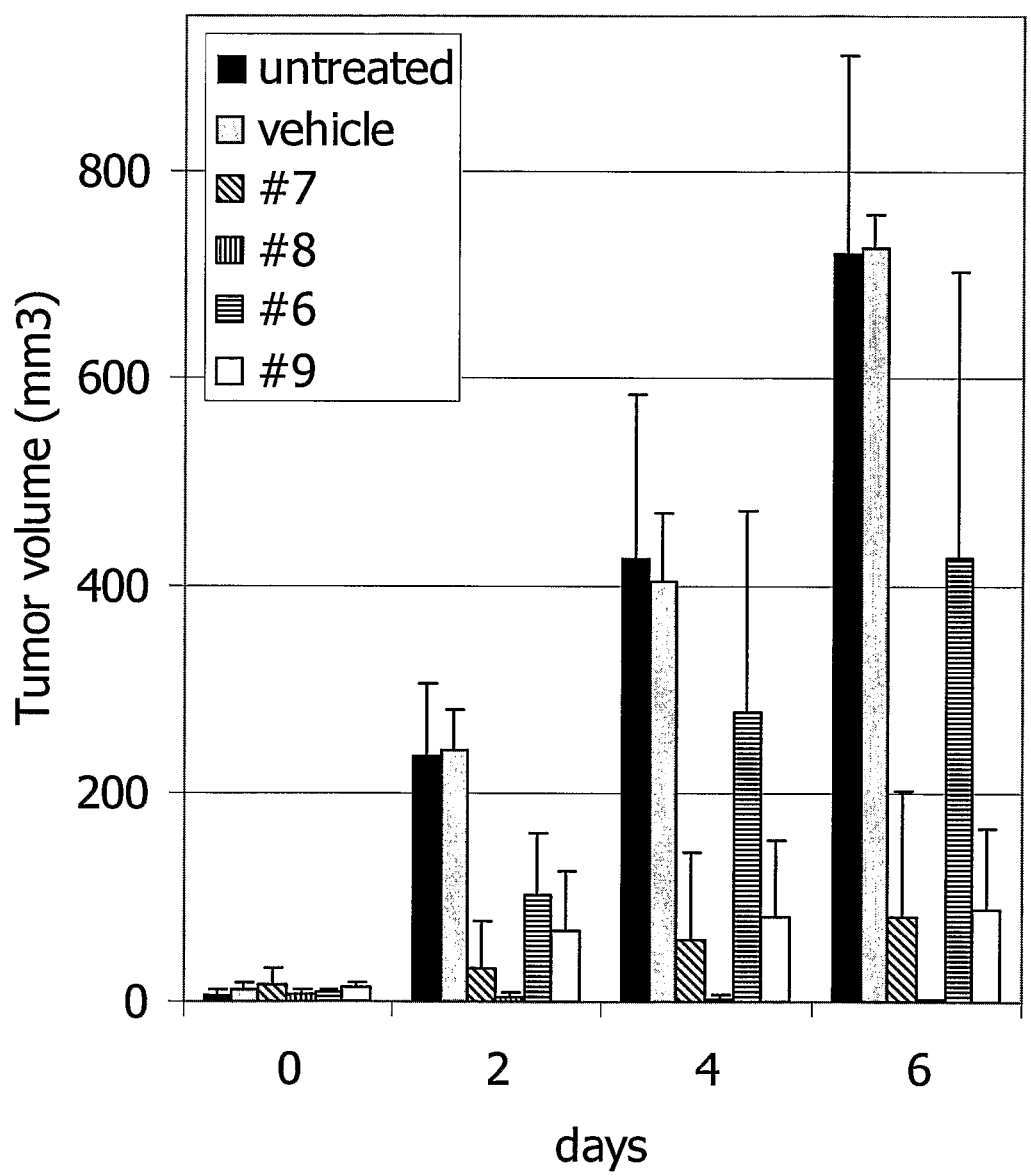
FIG. 13 shows the high efficacy of compounds 7, 8, and 9 as compared to compound 6 in growth inhibition of ovarian cancer A2780 tumors in nude mice model.

Since IGF1R is reported to be involved in many types of cancers, the sensitivity of a panel of cancer cell lines as well as several other analogs to compound 7, was screened in-vitro (table 3). Based on this screen, the efficacy of compounds 7 & 8 in ovarian cancer A2780 model was examined. FIG. 12 shows that IP administration of 20 mg/kg of either compound 7 or 8 once a day resulted in 87% inhibition of tumor growth. A comparative study of compounds 6, 7, 8 and 9 (administered IP once a day, 20 mg/kg) shows that compounds 7, 8 and 9 inhibit ovarian tumor growth by approximately 90% and even induce the regression of small tumors, whereas compound 6 administration (under the same conditions) resulted in 33% inhibition of tumor growth solely (FIG. 13).

Figure 17:
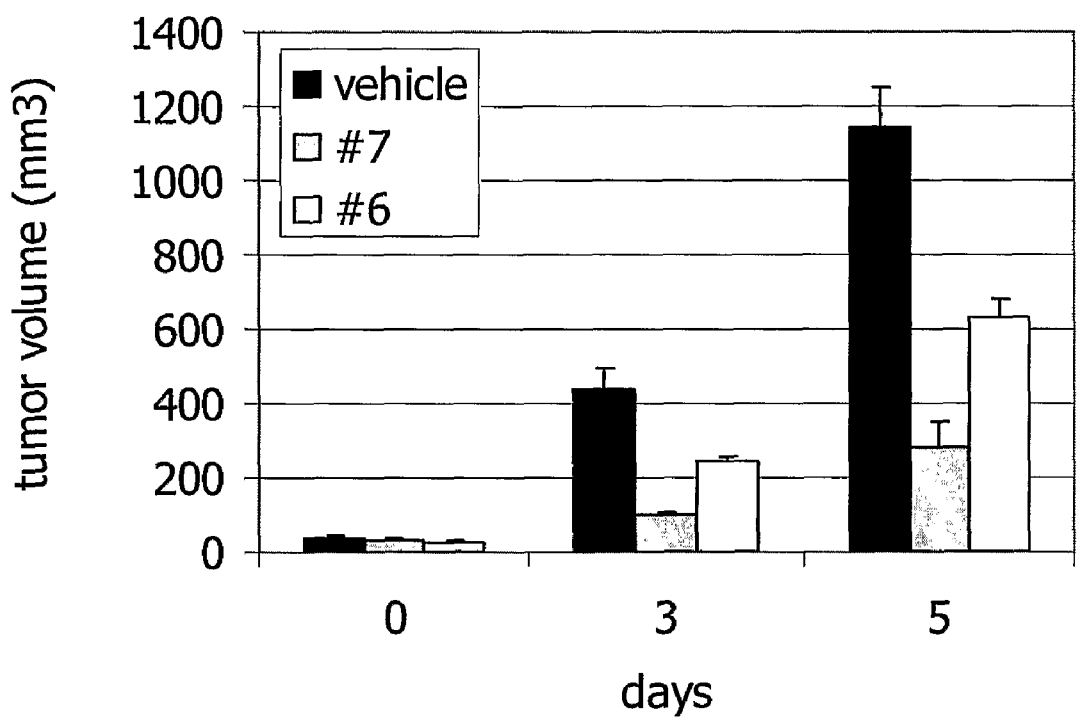
FIG. 17 shows the efficacy of compound 7 as compared to compound 6 in growth inhibition of melanoma B16 tumors in nude mice model. The inhibitors were administered IP at dose of 20 mg/kg, 1/day.
Figure 18:
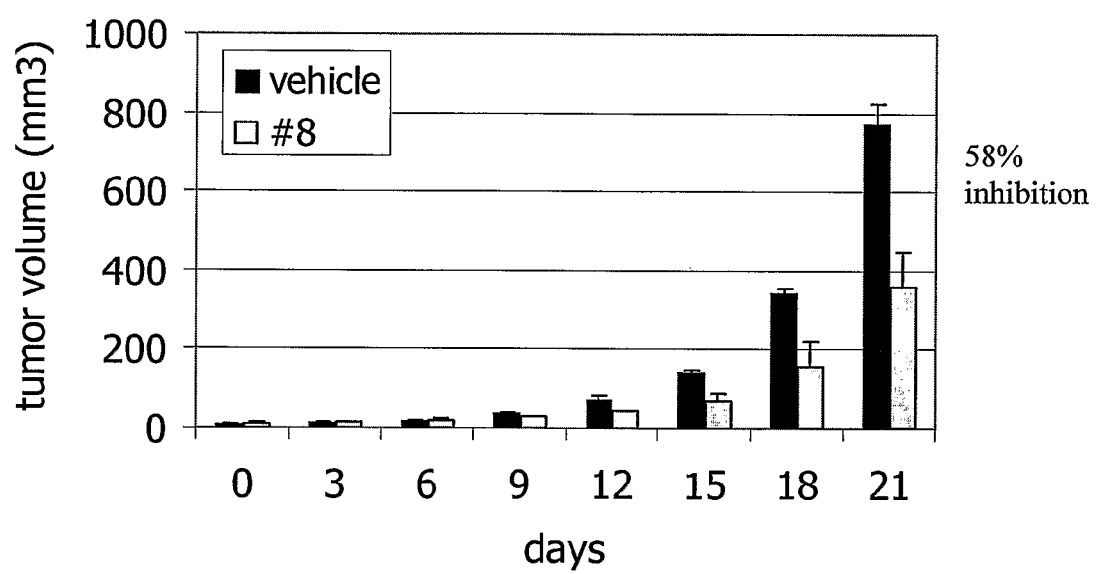
FIG. 18 shows the efficacy of compound 8 in growth inhibition of human melanoma YUMAC tumors in nude mice model. Compound 8 was administered IP at dose of 20 mg/kg, 1/day.

The efficacy of compounds 6 and 7 was tested on a melanoma B16 in-vivo model as well. Both molecules had a significant inhibitory effect with compound 7 being more efficient (FIG. 17). The efficacy of the compounds of the present invention on melanoma tumors was demonstrated also by the inhibition of the human metastatic melanoma YUMAC tumors in nude mice by compound 8 (FIG. 18).

Figure 14:
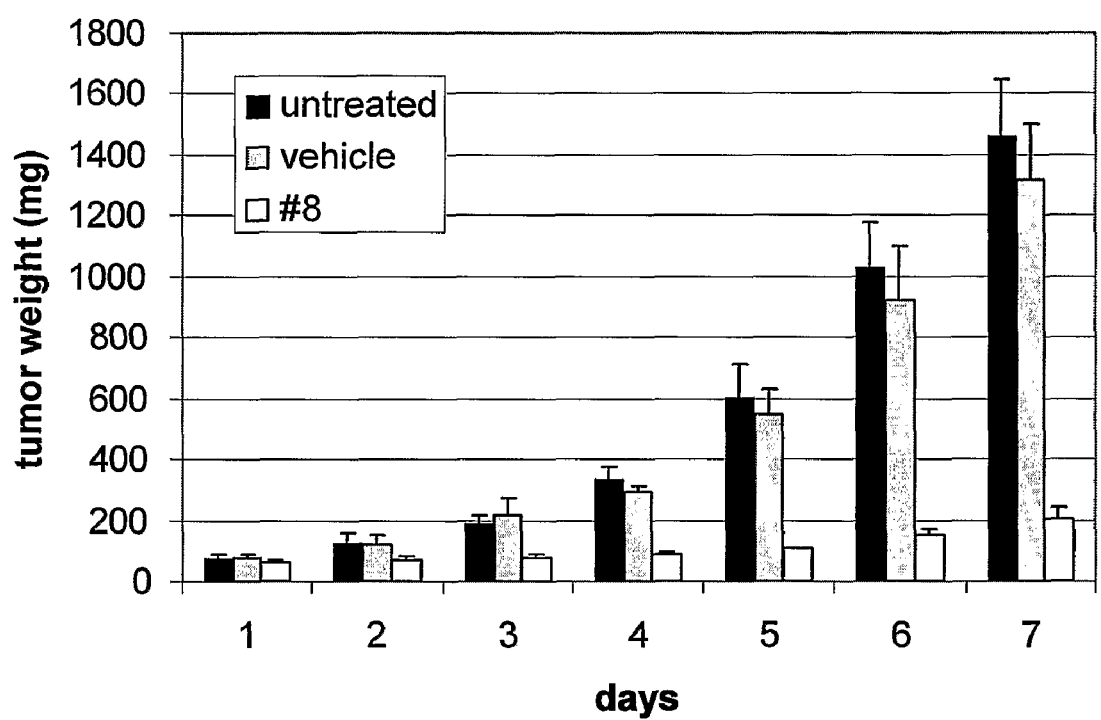
FIG. 14 shows that treatment of nude mice, bearing ovarian A2780 tumors larger than 50 mm$^3$, with compound 8 (IP, 1/day, 50 mg/kg) resulted in 82% growth inhibition of the tumors.
Figure 15:
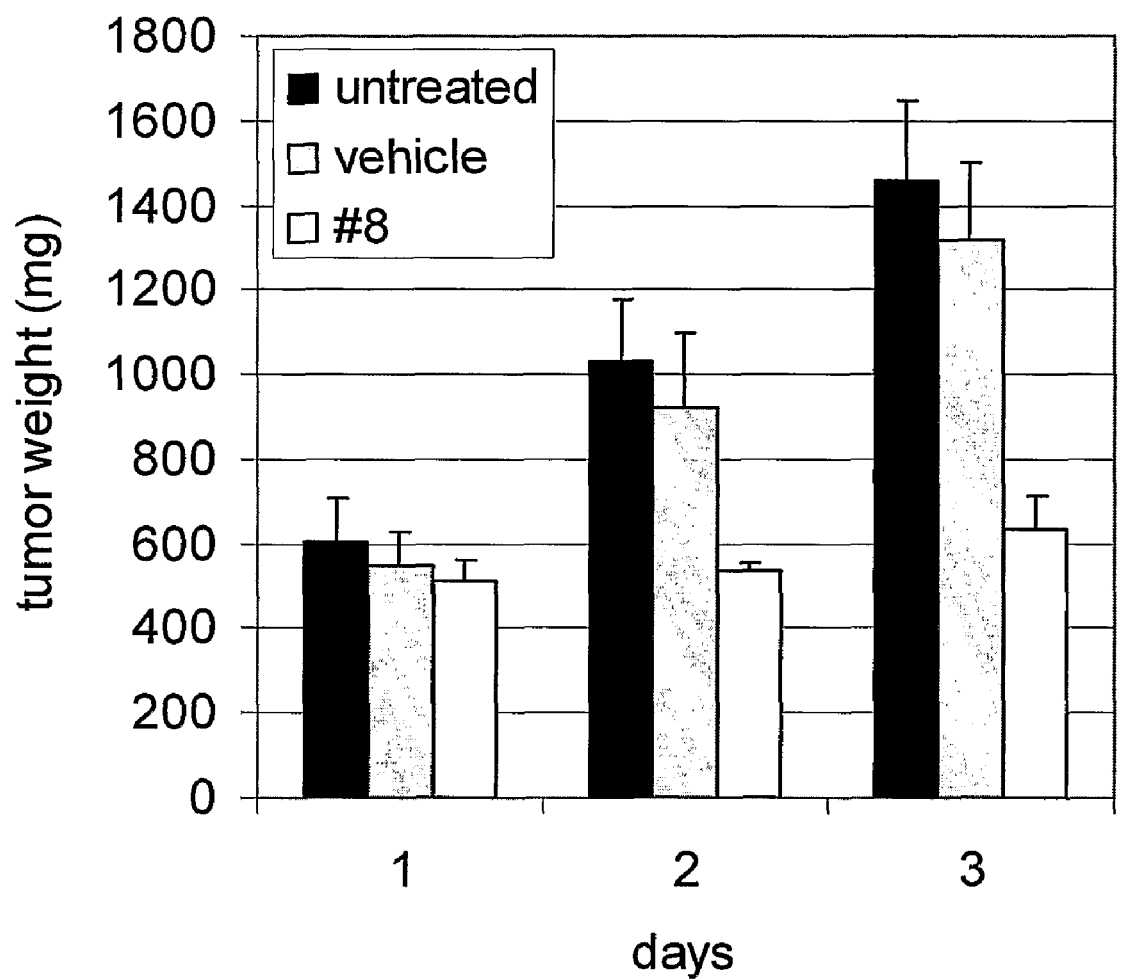
FIG. 15 shows that treatment of nude mice, bearing ovarian A2780 tumors larger than 470 mm$^3$, with compound 8 (IP, 1/day, 50 mg/kg) resulted in approximately 85% growth inhibition of the tumors.

Subsequently, the efficacy of compound 8 on inhibition of ovarian cancer A2780 tumor growth was examined. The administration began when the tumor size was larger than 50 mm³ or alternatively when the tumor size was larger than 470 mm³. FIGS. 14 & 15 show that IP administration of 50 mg/kg of compound 8 once a day resulted in a significant and dramatic inhibition of tumor growth. The compounds of the present invention were thus demonstrated as efficient anti-cancer agents for various cancers both in-vitro and in-vivo.

In-vitro Studies for Psoriasis

Figure 21:
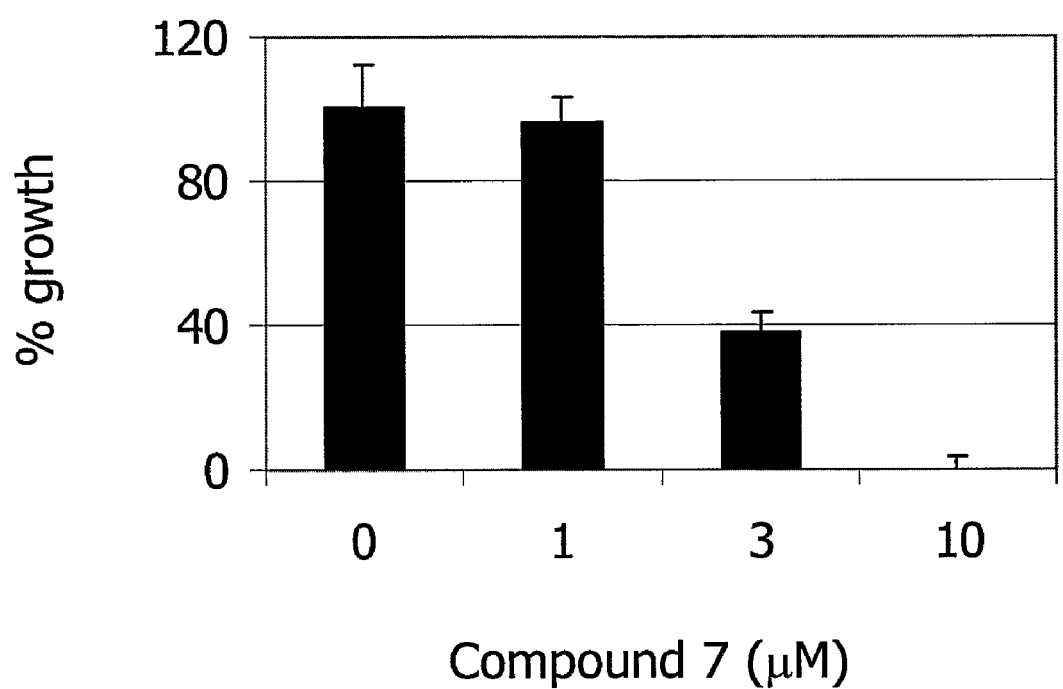
FIG. 21 shows a dose-dependent inhibition of primary keratinocytes growth by compound 7 (IC50=2.3 µM) in the presence of growth factor enriched medium.

Primary keratinocytes grown in enriched medium were demonstrated useful as an in-vitro model for psoriasis. Compound 7 inhibited the in vitro growth (IC50=2.3 μM) of primary keratinocytes, and is therefore a candidate as an antipsoriatic agent (FIG. 21).

Biochemical Characterization of Compound 6

Inhibition of the Tyrosine Kinase Activity of IGF1R and EGFR in Cells

Figure 19A:
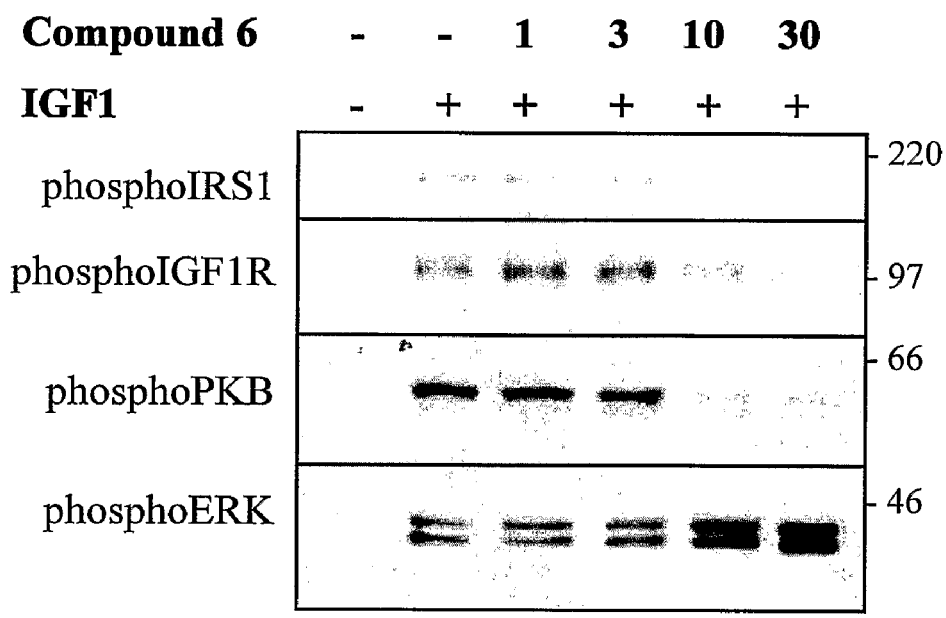
FIGS. 19A and 19B show the effect of compound 6 on MCF7 cells.
Figure 19B:
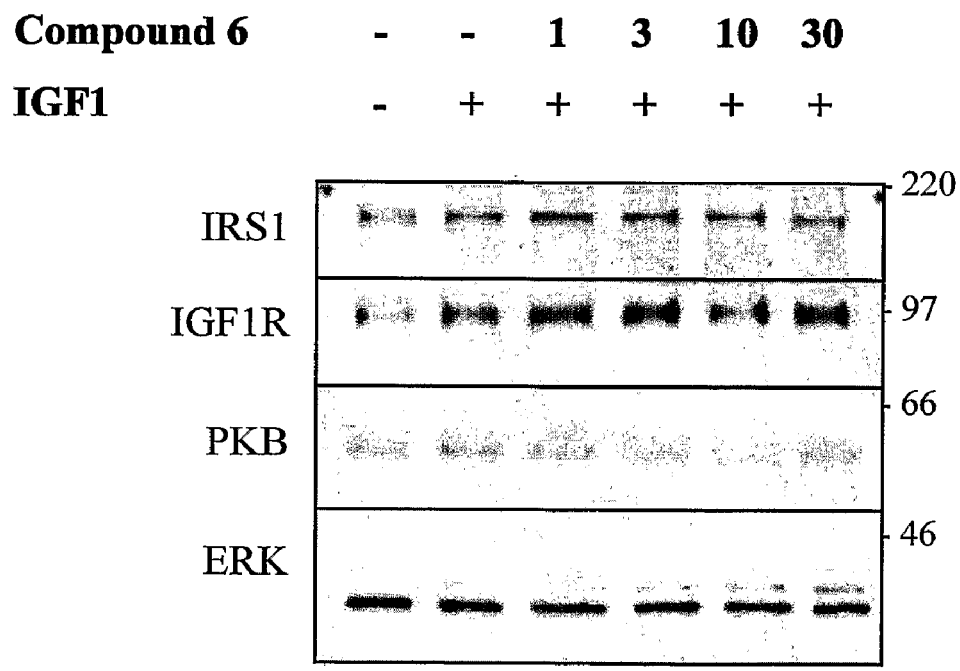
Figure 20A:
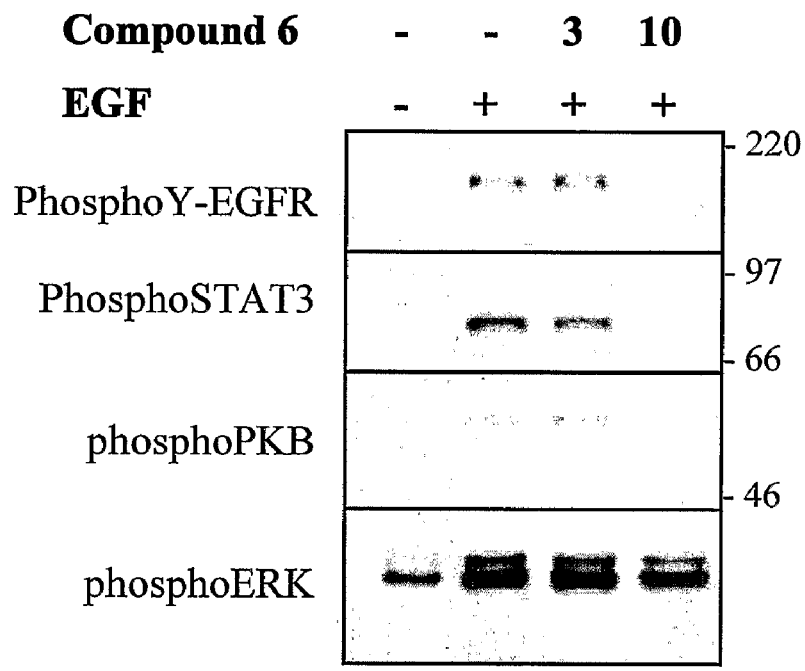
FIGS. 20A and 20B show the effect of compound 6 on EGFR activity in HRPC PC3 cells.
Figure 20B:
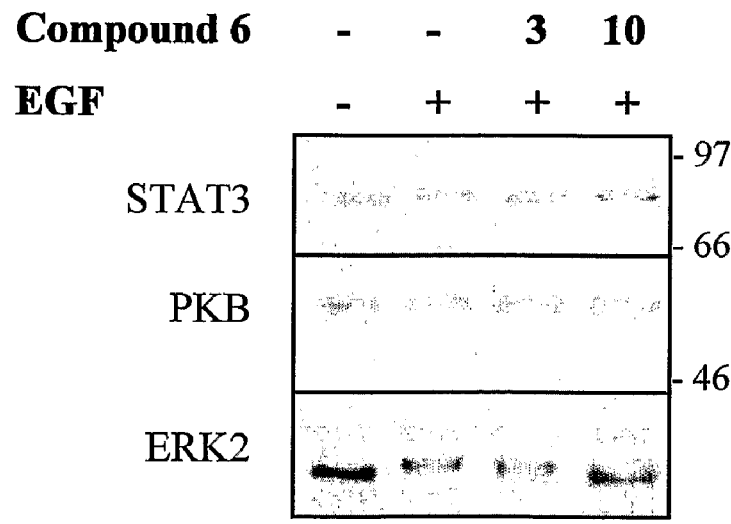

Exposure of breast cancer MCF7 cells to compound 6 yielded a significant inhibition of IGF1-induced signaling. FIG. 19A shows that compound 6 inhibited the autophosphorylation of IGF1R, the IGF1-induced tyrosine phosphorylation of IRS1 (a direct substrate of IGF1R), and the IGF1-induced activation of the Akt/PKB. As opposed to compound 7, compound 6 has no effect on either the IGF1R or the IRS1 levels (FIG. 19B). Compound 6 inhibited also EGFR and EGF-induced tyrosine phosphorylation of STAT3, a direct substrate of EGFR, and the EGF-induced activation of the PKB pathway (FIGS. 20A & 20B).

Growth Inhibition

Exposure of various cancer cells to compound 6 caused a significant inhibition of colony formation both in soft agar and in plates (table 3, clonogenic assay).

While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A compound represented by the structure of formula 1:

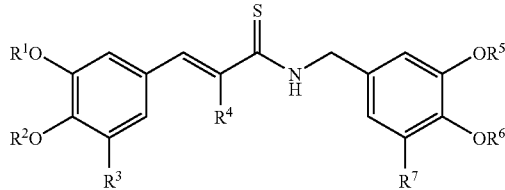

wherein
 $R^1$, $R^2$, $R^5$ and $R^6$ are independently selected from H, $C_1$-$C_4$ alkyl, acyl and a functional group that gives rise to hydroxyl upon hydrolysis;
 $R^3$ and $R^7$ are independently selected from H, halogen, haloalkyl and $OR^8$ wherein $R^8$ is H, $C_1$-$C_4$ alkyl, acyl or a functional group that gives rise to hydroxyl upon hydrolysis;
 $R^4$ is H or CN,
 including salts, hydrates, solvates, polymorphs, optical isomers, geometrical isomers, enantiomers, diastereomers, and mixtures thereof.

2. A compound according to claim 1, wherein $R^4$ is CN.

3. A compound according to claim 2, wherein $R^1$, $R^2$, $R^5$ and $R^6$ are each hydrogen; or wherein $R^1$, $R^2$, $R^5$ and $R^6$ are each $CH_3$.

4. A compound according to claim 2, wherein $R^3$ and $R^7$ are each a hydrogen, halogen, halomethyl, OH or $OCH_3$.

5. A compound of claim 2, wherein $R^1$, $R^2$, $R^5$ and $R^6$ are each H and $R^3$ is halogen and $R^7$ is OH; or
 $R^3$ and $R^7$ are each halogen; or
 $R^3$ is halomethyl and $R^7$ is OH; or
 $R^3$ is halogen and $R^7$ is H; or
 $R^3$ is OH and $R^7$ is halogen.

6. A compound of claim 2, wherein $R^1$, $R^2$, $R^5$ and $R^6$ are each $CH_3$, and $R^3$ is halogen and $R^7$ is $OCH_3$; or
 $R^3$ and $R^7$ are each halogen.

7. A compound according to claim 1, wherein $R^4$ is hydrogen.

8. A compound according to claim 7, wherein $R^1$, $R^2$, $R^5$ and $R^6$ are each hydrogen; or wherein $R^1$, $R^2$, $R^5$ and $R^6$ are each $CH_3$.

9. A compound according to claim 7, wherein $R^3$ and $R^7$ are each hydrogen, halogen, halomethyl, OH or $OCH_3$.

10. A compound of claim 7, wherein $R^1$, $R^2$, $R^5$ and $R^6$ are each H, and $R^3$ is halogen and $R^7$ is OH; or
 $R^3$ and $R^7$ are each halogen; or
 $R^3$ is halomethyl and $R^7$ is OH; or
 $R^3$ is halogen and $R^7$ is H; or
 $R^3$ is OH and $R^7$ is halogen.

11. A compound of claim 7, wherein $R^1$, $R^2$, $R^5$ and $R^6$ are each $CH_3$, and $R^3$ is halogen and $R^7$ is $OCH_3$; or
 $R^3$ and $R^7$ are each halogen.

12. A compound selected from the group consisting of:

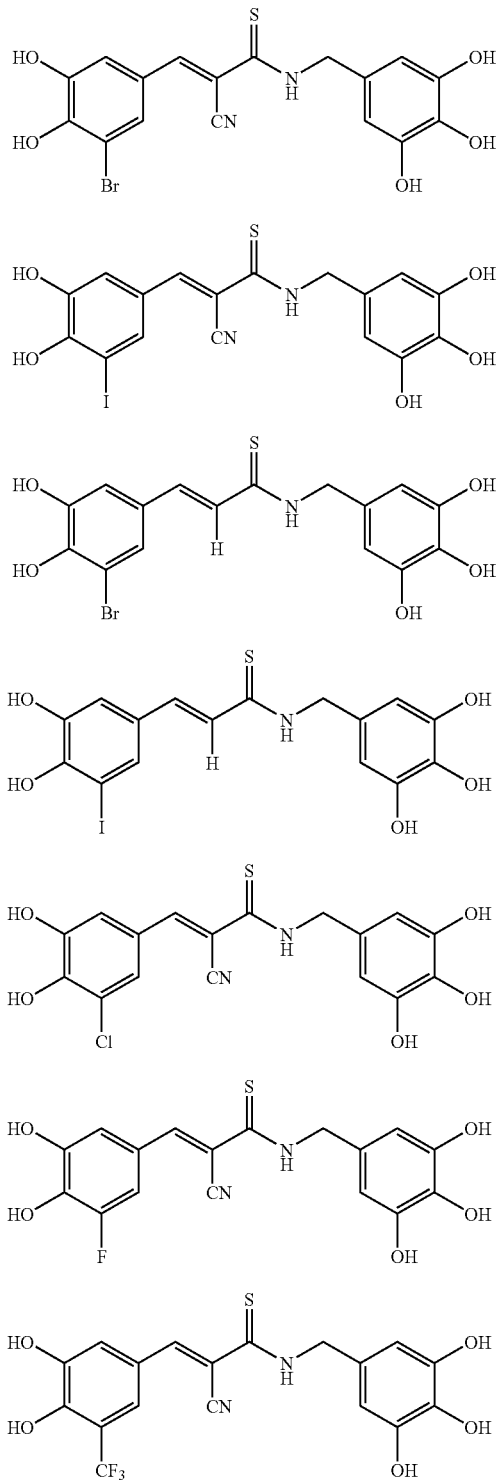
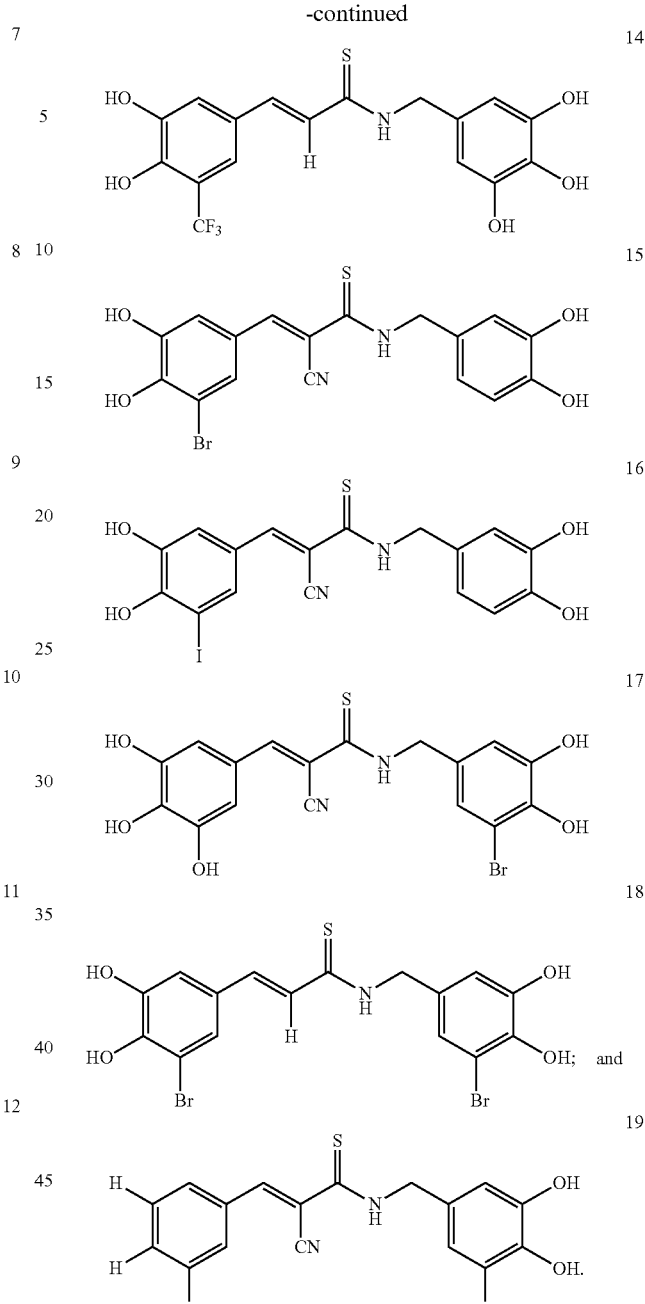
13. A pharmaceutical composition, comprising a therapeutically effective amount of compound of claim 1, and a pharmaceutically acceptable carrier or excipient.
14. A pharmaceutical composition, comprising a therapeutically effective amount of compound of claim 12, and a pharmaceutically acceptable carrier or excipient.
* * * * *